US012349869B2

(12) United States Patent
Jensen et al.

(10) Patent No.: US 12,349,869 B2
(45) Date of Patent: Jul. 8, 2025

(54) ARTICULATED TIP PART FOR AN ENDOSCOPE

(71) Applicant: AMBU A/S, Ballerup (DK)

(72) Inventors: Thomas Bachgaard Jensen, Copenhagen V (DK); Kaspar Mat Matthison-Hansen, Helsingør (DK); Jan Guldberg Hansen, Greve (DK); Troels Nicolaj Qvist, Roskilde (DK); Michael Kappler Hansen, Vallensæk (DK)

(73) Assignee: AMBU A/S, Ballerup (DK)

( * ) Notice: Subject to any disclaimer, the term of this patent is extended or adjusted under 35 U.S.C. 154(b) by 707 days.

(21) Appl. No.: 16/874,628

(22) Filed: May 14, 2020

(65) Prior Publication Data

US 2020/0268238 A1 Aug. 27, 2020

Related U.S. Application Data

(63) Continuation-in-part of application No. 16/807,283, filed on Mar. 3, 2020, now abandoned, and a
(Continued)

(30) Foreign Application Priority Data

Dec. 21, 2018 (EP) ...................................... 18215278
Mar. 4, 2019 (EP) ...................................... 19160528

(51) Int. Cl.
*A61B 1/005* (2006.01)
*A61B 1/00* (2006.01)
*A61B 1/05* (2006.01)

(52) U.S. Cl.
CPC ........ *A61B 1/0055* (2013.01); *A61B 1/00009* (2013.01); *A61B 1/00045* (2013.01);
(Continued)

(58) Field of Classification Search
CPC ..... A61B 1/005; A61B 1/0051; A61B 1/0052; A61B 1/0053; A61B 1/0055;
(Continued)

(56) References Cited

U.S. PATENT DOCUMENTS 4,580,551 A 4/1986 Siegmund et al.
4,651,718 A 3/1987 Collins
(Continued)

FOREIGN PATENT DOCUMENTS

CN 103228199 A 7/2013
EP 0 183 585 6/1986
(Continued)

OTHER PUBLICATIONS

Non-final Office action in U.S. Appl. No. 16/718,335, dated Nov. 24, 2021, 26 pages.
(Continued)

*Primary Examiner* — Ryan N Henderson
(74) *Attorney, Agent, or Firm* — Faegre Drinker Biddle & Reath LLP

(57) ABSTRACT

A medical device operable to obtain images of an internal cavity of a patient, including a handle; a flexible tube including a first section having a first radial cross-section area and a second section distal of the first section and having a second radial cross-section area smaller than the first radial cross-section area, the second section having an outer surface; a bending section extending from the flexible tube and including a proximal end segment, a distal end segment, and intermediate segments between the proximal end segment and the distal end segment, the intermediate segments hingedly connected to each other, the proximal end segment including a proximal end segment peripheral wall defining an internal space, wherein the second section is positioned at least partly in the internal space; and a
(Continued)

camera assembly supported by the bending section and operable to generate images of distal views.

18 Claims, 16 Drawing Sheets

Related U.S. Application Data continuation-in-part of application No. 16/718,335, filed on Dec. 18, 2019, now Pat. No. 11,992,181.

(52) U.S. Cl.
CPC ...... *A61B 1/00071* (2013.01); *A61B 1/00137* (2013.01); *A61B 1/00165* (2013.01); *A61B 1/005* (2013.01); *A61B 1/0052* (2013.01); *A61B 1/05* (2013.01)

(58) Field of Classification Search
CPC ..... A61B 1/0056; A61B 1/057; A61B 1/0058; A61B 2017/003; A61B 2017/00305; A61B 2017/00309; A61B 2017/00314; A61B 2017/00318; A61B 2017/00323; A61B 2017/00327; A61M 25/0133; A61M 25/0136; A61M 25/0138; A61M 25/0141; A61M 25/0144; A61M 25/0147; A61M 25/0152; A61M 25/0155; A61M 25/0158
See application file for complete search history.

(56) References Cited

U.S. PATENT DOCUMENTS

| | | | |
|---|---|---|---|
| 4,706,653 A | 11/1987 | Yamamoto | |
| 4,745,470 A | 5/1988 | Yabe et al. | |
| 4,778,247 A | 10/1988 | Carpenter | |
| 4,805,596 A * | 2/1989 | Hatori | A61B 1/0057 600/142 |
| 4,832,003 A | 5/1989 | Yabe | |
| 4,841,952 A * | 6/1989 | Sato | A61B 1/0051 600/141 |
| 4,856,495 A | 8/1989 | Tohjoh et al. | |
| 4,860,732 A | 8/1989 | Hasegawa et al. | |
| 4,911,148 A | 3/1990 | Sosnowski et al. | |
| 4,918,521 A | 4/1990 | Yabe et al. | |
| 5,089,895 A | 2/1992 | Fraker et al. | |
| 5,176,126 A | 1/1993 | Chikama | |
| 5,251,611 A * | 10/1993 | Zehel | A61B 1/0055 600/114 |
| 5,376,960 A | 12/1994 | Wurster | |
| 5,379,756 A | 1/1995 | Pileski et al. | |
| 5,386,816 A * | 2/1995 | Inoue | A61B 1/0055 600/149 |
| 5,418,566 A | 5/1995 | Kameishi | |
| 5,438,975 A | 8/1995 | Miyagi et al. | |
| 5,547,457 A | 8/1996 | Tsuyuki et al. | |
| 5,685,825 A * | 11/1997 | Takase | A61B 1/0055 528/59 |
| 5,762,631 A | 6/1998 | Klein | |
| 5,830,401 A | 11/1998 | Prichard et al. | |
| 5,966,168 A | 10/1999 | Miyazaki | |
| 6,004,263 A | 12/1999 | Nakaichi | |
| 6,110,104 A | 8/2000 | Suzuki et al. | |
| 6,302,616 B1 | 10/2001 | Takahashi | |
| 6,456,863 B1 | 9/2002 | Levin et al. | |
| 6,551,239 B2 * | 4/2003 | Renner | A61B 1/00075 600/139 |
| 6,991,603 B2 * | 1/2006 | Krupa | A61B 1/0055 138/119 |
| 7,455,806 B2 | 11/2008 | Junger et al. | |
| 7,682,319 B2 * | 3/2010 | Martin | A61B 18/1492 604/165.01 |
| 7,758,495 B2 | 7/2010 | Pease et al. | |
| 8,182,422 B2 | 5/2012 | Bayer et al. | |
| 8,547,424 B2 | 10/2013 | Ishii et al. | |
| 8,790,250 B2 | 7/2014 | Petersen et al. | |
| 9,125,582 B2 | 9/2015 | Petersen | |
| 9,220,400 B2 | 12/2015 | Petersen | |
| 9,345,390 B2 * | 5/2016 | Matsuo | A61B 1/0055 |
| 9,486,595 B2 | 11/2016 | Borrye et al. | |
| 9,572,482 B2 | 2/2017 | Lin | |
| 9,622,649 B2 | 4/2017 | Lin | |
| 10,321,804 B2 | 6/2019 | Jacobsen et al. | |
| 11,357,386 B2 | 6/2022 | Lund et al. | |
| 2001/0029317 A1 * | 10/2001 | Hayakawa | A61L 29/08 600/140 |
| 2001/0056224 A1 * | 12/2001 | Renner | A61B 1/00075 600/139 |
| 2002/0010385 A1 * | 1/2002 | Ishibiki | A61B 1/0105 600/130 |
| 2002/0022765 A1 | 2/2002 | Belson | |
| 2002/0026095 A1 * | 2/2002 | Sakamoto | A61B 1/0055 600/142 |
| 2003/0056540 A1 | 3/2003 | Mukasa et al. | |
| 2003/0216616 A1 * | 11/2003 | Krupa | A61B 1/0055 600/920 |
| 2004/0044350 A1 * | 3/2004 | Martin | A61B 18/1492 606/139 |
| 2004/0143276 A1 | 7/2004 | Sturtz et al. | |
| 2004/0199052 A1 | 10/2004 | Banik et al. | |
| 2004/0242963 A1 | 12/2004 | Matsumoto | |
| 2005/0070759 A1 | 3/2005 | Armstrong | |
| 2005/0075538 A1 | 4/2005 | Banik et al. | |
| 2005/0107667 A1 * | 5/2005 | Danitz | A61B 34/70 600/139 |
| 2005/0131279 A1 | 6/2005 | Boulais | |
| 2005/0140068 A1 | 6/2005 | Junger et al. | |
| 2005/0154262 A1 | 7/2005 | Banik et al. | |
| 2005/0119527 A1 | 9/2005 | Ellis et al. | |
| 2005/0203341 A1 | 9/2005 | Welker et al. | |
| 2005/0226682 A1 * | 10/2005 | Chersky | A61B 1/00149 403/56 |
| 2005/0234499 A1 | 10/2005 | Olson et al. | |
| 2006/0173243 A1 * | 8/2006 | Watanabe | A61B 1/04 600/141 |
| 2006/0178556 A1 | 8/2006 | Hasser et al. | |
| 2006/0235276 A1 * | 10/2006 | Takase | A61B 1/00174 600/177 |
| 2006/0235457 A1 | 10/2006 | Belson | |
| 2007/0043261 A1 * | 2/2007 | Watanabe | A61B 1/00071 600/152 |
| 2007/0049800 A1 | 3/2007 | Boulais | |
| 2007/0129466 A1 | 6/2007 | Kagawa et al. | |
| 2007/0225555 A1 * | 9/2007 | Stefanchik | A61B 17/3415 600/104 |
| 2007/0249896 A1 | 10/2007 | Goldfarb et al. | |
| 2007/0249907 A1 | 10/2007 | Boulais et al. | |
| 2008/0114205 A1 | 5/2008 | Kagawa et al. | |
| 2008/0194911 A1 | 8/2008 | Lee | |
| 2008/0221393 A1 | 9/2008 | Padget | |
| 2008/0249483 A1 | 10/2008 | Slenker | |
| 2008/0268559 A1 | 10/2008 | Jung | |
| 2008/0287741 A1 | 11/2008 | Ostrovsky | |
| 2009/0054728 A1 | 2/2009 | Trusty | |
| 2009/0093679 A1 * | 4/2009 | Suigetsu | A61B 1/00128 600/139 |
| 2009/0177040 A1 | 7/2009 | Lyons | |
| 2009/0209819 A1 | 8/2009 | Kitagawa et al. | |
| 2010/0210905 A1 | 8/2010 | Takeuchi et al. | |
| 2010/0217082 A1 | 8/2010 | Ito et al. | |
| 2010/0262180 A1 | 10/2010 | Danitz et al. | |
| 2010/0280316 A1 | 11/2010 | Dietz et al. | |
| 2010/0324367 A1 | 12/2010 | Matsumoto et al. | |
| 2011/0034771 A1 | 2/2011 | Konstorum | |
| 2011/0230718 A1 | 9/2011 | Akui | |
| 2011/0251519 A1 | 10/2011 | Romoscanu | |
| 2011/0295065 A1 * | 12/2011 | Gurusamy | A61B 1/0057 600/141 |
| 2011/0306831 A1 * | 12/2011 | Kohnke | A61B 1/0055 600/109 |
| 2012/0002981 A1 | 2/2012 | Frassica et al. | |

(56) References Cited

U.S. PATENT DOCUMENTS

| | | | |
|---|---|---|---|
| 2012/0029281 A1 | 2/2012 | Frassica et al. | |
| 2012/0165608 A1 | 6/2012 | Banik et al. | |
| 2012/0215068 A1* | 8/2012 | Furuta | A61B 1/0051 600/125 |
| 2013/0197484 A1* | 8/2013 | Seddon | A61M 39/12 604/533 |
| 2013/0245376 A1* | 9/2013 | Oku | A61B 1/0011 600/129 |
| 2013/0331730 A1 | 12/2013 | Fenech et al. | |
| 2014/0114129 A1 | 4/2014 | Peh | |
| 2014/0142388 A1 | 5/2014 | Suzuki | |
| 2014/0243592 A1 | 8/2014 | Kato et al. | |
| 2014/0296636 A1* | 10/2014 | Hatano | A61B 1/00124 600/138 |
| 2015/0005580 A1 | 1/2015 | Petersen | |
| 2015/0216589 A1 | 8/2015 | Wittenberger et al. | |
| 2015/0335227 A1* | 11/2015 | Jacobsen | A61B 1/0008 600/110 |
| 2015/0366436 A1 | 12/2015 | Iuel | |
| 2016/0085063 A1* | 3/2016 | Miller | G02B 23/26 385/31 |
| 2016/0101254 A1 | 4/2016 | Hansen | |
| 2016/0249788 A1 | 9/2016 | Saito et al. | |
| 2016/0278617 A1* | 9/2016 | Okaniwa | A61B 1/0052 |
| 2016/0345806 A1 | 12/2016 | Ishii et al. | |
| 2017/0028684 A1 | 2/2017 | Imai et al. | |
| 2017/0038580 A1 | 2/2017 | Okazaki et al. | |
| 2018/0317751 A1* | 11/2018 | Kuboi | A61B 1/00006 |
| 2019/0223694 A1 | 7/2019 | Lund et al. | |
| 2020/0022563 A1 | 1/2020 | Sugita | |
| 2020/0100662 A1 | 4/2020 | Jensen et al. | |
| 2020/0138268 A1 | 5/2020 | Matthison-Hansen et al. | |
| 2020/0196835 A1 | 6/2020 | Qvist et al. | |
| 2020/0281445 A1 | 9/2020 | Matthison-Hansen et al. | |

FOREIGN PATENT DOCUMENTS

| | | |
|---|---|---|
| EP | 1927312 A1 | 6/2008 |
| EP | 2949262 A1 | 12/2015 |
| JP | H06-189898 | 7/1994 |
| JP | 2 948722 | 9/1999 |
| JP | 2002-224019 | 8/2002 |
| JP | 2005-152043 A | 6/2005 |
| KR | 10-2012-0056363 A | 6/2012 |
| WO | 2007/124211 A2 | 11/2007 |
| WO | 2009/029639 A1 | 3/2009 |
| WO | 2010/066787 A1 | 6/2010 |
| WO | 2010/066788 A2 | 6/2010 |
| WO | 2010/066789 A1 | 6/2010 |
| WO | 2010/066790 A1 | 6/2010 |
| WO | 2010/067765 A1 | 6/2010 |
| WO | 2014/106510 A1 | 7/2014 |
| WO | 2014/106511 A1 | 7/2014 |
| WO | 2016/188537 A1 | 12/2016 |
| WO | 2016/188538 A1 | 12/2016 |
| WO | 2016/188539 A1 | 12/2016 |
| WO | 2016/188540 A1 | 12/2016 |
| WO | 2016/188541 A1 | 12/2016 |
| WO | 2016/188542 A1 | 12/2016 |
| WO | 2016/188543 A1 | 12/2016 |

OTHER PUBLICATIONS

Office Action issued in European Patent Application No. 19160528, dated Feb. 3, 2023.
Final office action in U.S. Appl. No. 16/718,335, dated Sep. 7, 2022.
Extended Search Report in related EPO application No. EP 18 215 278 dated Jun. 5, 2019, 7 pages.
Extended Search Report in related EPO application No. EP 19 160 528 dated Sep. 2, 2019, 7 pages.
Exam Report issued in Denmark Patent App. No. 2017 70501, dated Nov. 27, 2017, 9 pages.
In corresponding International Application No. PCT/DK2013/050002, International Search Report, dated Sep. 12, 2013; 2 pages and International Preliminary Report on Patentability; dated Jul. 7, 2015; 7 pages.
International Preliminary Report on Patentability received for PCT Patent Application No. PCT/DK2013/050002, dated Jul. 16, 2015, 8 pages.
International Preliminary Report on Patentability received for PCT Patent Application No. PCT/EP2018/066916, dated Jan. 9, 2020, 7 pages.
International Search Report and Written Opinion received for PCT Patent Application No. PCT/DK2013/050002, dated Sep. 12, 2013, 9 pages.
International Search Report in related PCT application No. PCT/EP2018/0066916 dated Oct. 10, 2018, 3 pages.
Office Action issued in European Patent Application No. 18215278.5, dated Nov. 28, 2022, Nov. 28, 2022.
Final Office Action received for U.S. Appl. No. 16/807,283, dated May 2, 2024, 23 pages.
Office Action issued Aug. 16, 2024 in U.S. Appl. No. 16/807,283 (14 pages).

* cited by examiner

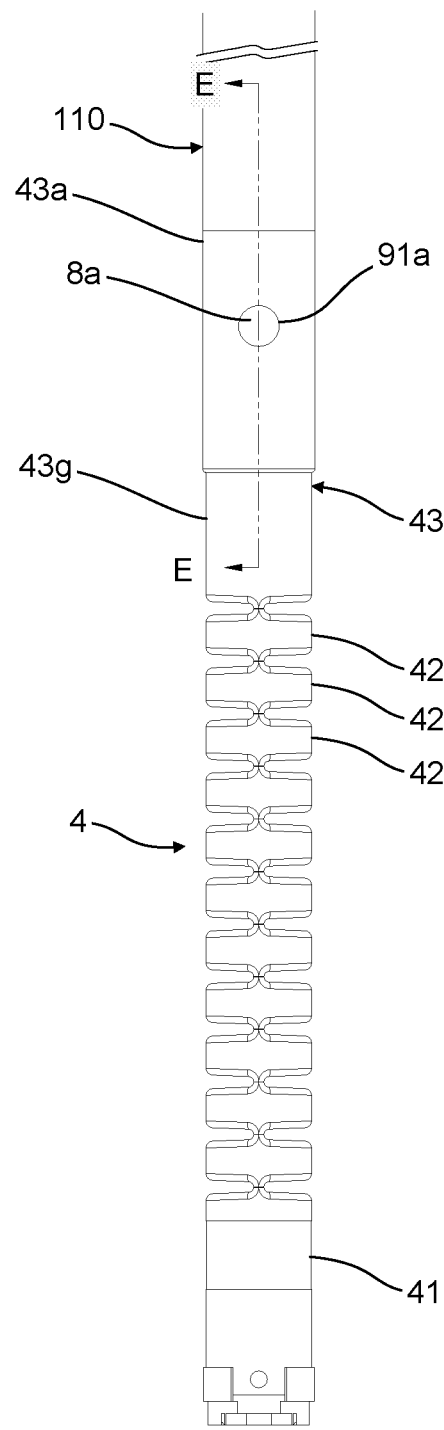
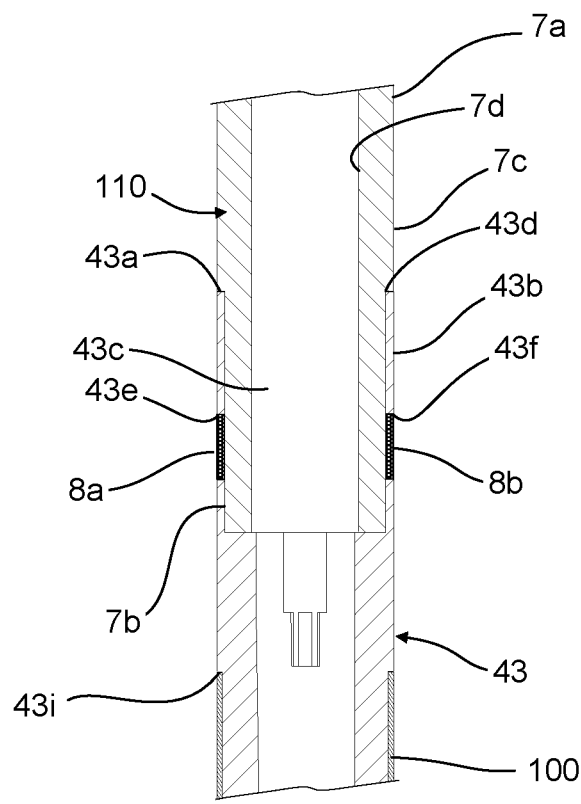
Fig. 11a
Fig. 11b

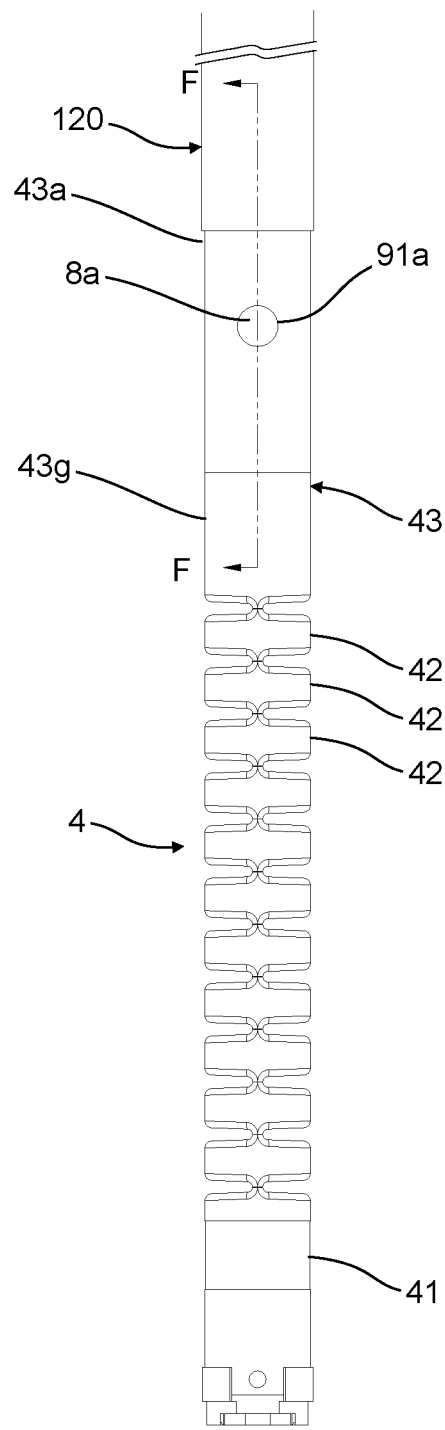
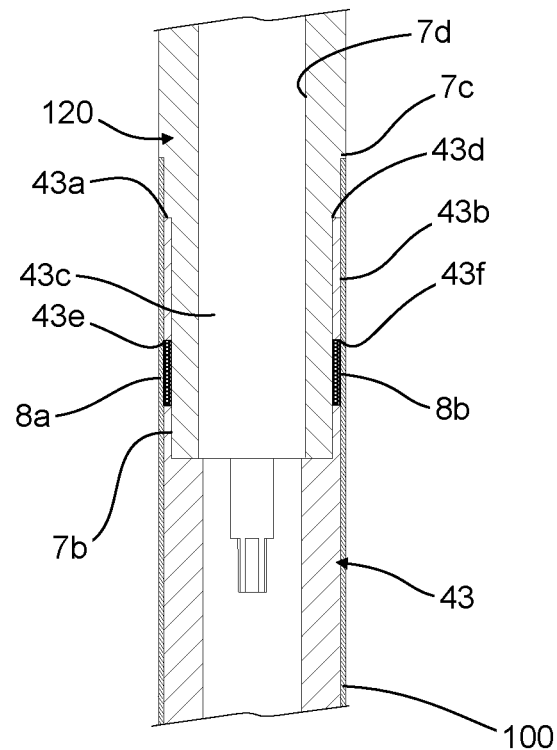
Fig. 13a
Fig. 13b

ARTICULATED TIP PART FOR AN ENDOSCOPE

CROSS-REFERENCE TO RELATED APPLICATIONS

This application is a continuation-in-part of U.S. patent application Ser. No. 16/718,335, filed Dec. 18, 2019, which claims priority from European Patent Application No. 18215278.5, filed on Dec. 21, 2018 and is a continuation-in-part of U.S. patent application Ser. No. 16/807,283, filed Mar. 3, 2020, which claims priority from European Patent Application No. 19160528.6, filed Mar. 4, 2019; said applications are incorporated herein by reference in their entirety.

TECHNICAL FIELD

The present specification relates to medical devices with cameras, such as endoscopes, and more specifically to the articulated tip of the medical device.

BACKGROUND

Endoscopes are well known for visually inspecting inaccessible places such as human body cavities. Typically, the endoscope comprises an elongated insertion tube with a handle at the proximal end, as seen from the operator, and visual inspection means, such as a built-in camera, at the distal end of the elongated insertion tube. This definition of the terms distal and proximal, i.e. proximal being the end closest to the operator and distal being the end remote from the operator, as used herein for endoscopes in general, is adhered to in the present specification.

As the name indicates, endoscopes are used for seeing inside things, such as lungs or other human body cavities of a patient. Modern endoscopes are therefore typically equipped with a light source and a vision receptor including a vision sensor, such as a camera or an image sensor. Provided that sufficient light is present, it is possible for the operator to see where the endoscope is steered and to set the target of interest once the tip has been advanced thereto. This therefore normally requires illumination of the area in front of the distal tip of the endoscope, in particular the field of vision of the camera(s). The light source, such as a light emitting diode or an optical fibre, may provide illumination.

Electrical wiring for the camera and other electronics, such as LED lighting accommodated in the tip part at the distal end, run along the inside of the elongated insertion tube from the handle to the tip part. Instead of using cameras, endoscopes may also be fibre-optic, in which case the optical fibres run along the inside of the elongated insertion tube to the tip part. For some applications, a working or suction channel may run along the inside of the insertion tube from the handle to the tip part, e.g. allowing liquid to be removed from the body cavity or allowing for insertion of surgical instruments or the like, into the body cavity. The suction channel may be connected to a suction connector, typically positioned at a handle at the proximal end of the insertion tube. For other applications, the working or suction channel may be omitted.

To manoeuvre the endoscope inside the body cavity, the distal end of the endoscope may comprise a bending section with increased flexibility, e.g. an articulated tip part allowing the operator to bend this section. Typically this is done by tensioning or slacking steering wires also running along the inside of the elongated insertion tube from the articulated tip part to a control mechanism of the handle.

In an insertion tube for single-use endoscopes, the preferred way of assembling the parts of the insertion tube is by adhesion as this is low-cost, improves liquid tightness, and flexible as adhesion can typically be implemented with a wide range of part geometries. However, the bending section is generally made of an elastic polyolefin material to allow sufficient elasticity for a high quality manoeuvering of the endoscope, while still keeping material costs low to allow the manufacture of a single-use endoscope. A drawback of this group of materials is that they are usually difficult to adhere to, and thus presents a challenge when assembling the parts of the endoscope.

An example of an endoscope is disclosed in commonly owned U.S. Pat. No. 10,321,804. This document discloses an articulated tip part with a proximal end segment having a number of recesses or cut-outs in the surface for aiding in securing the articulated tip member to the insertion tube of the endoscope.

Another example of a steerable endoscope is described in commonly owned U.S. Patent Publication No. 2019/0223694. The steerable endoscope disclosed therein has an insertion tube with an internal working channel and a connector at the handle adapted for the attachment of a syringe. A recess is adapted to accommodate a cylindrical body of the syringe when the syringe is attached to the connector. The endoscope is adapted to perform bronchoalveolar lavage, a procedure for obtaining samples, through the working channel, of organic material from a lung segment of a patient.

The articulated tip part of the present disclosure is intended for use in a single-use or disposable endoscope, it is therefore desired to reduce cost including manufacturing cost. The preferred way of assembling the tip part is by adhesion as this is low-cost, improves liquid tightness, and can typically be implemented with a wide range of part geometries to produce a flexible tip part. The bending section is generally made of an elastic polyolefin material to allow sufficient elasticity for high quality maneuvering of the endoscope, while still keeping material costs low to allow the manufacture of a single-use endoscope. However, a shortcoming of this group of materials is that the materials are usually difficult to adhere to and thus present a challenge when assembling the parts of the endoscope.

It is therefore desirable to provide an improved tip part, and a method for obtaining the tip part, capable of eliminating or mitigating the shortcomings of prior tip parts and methods of obtaining the same.

SUMMARY

On this background, it may be seen as an object of the present specification to provide an improved articulated tip part for an endoscope.

The object may be met by the present embodiments as described in the following. It should be understood that, as used herein, the term "endoscope" is used broadly to denote a class of medical devices usable for examination of body openings, e.g. for exploration of a lung cavity, in a plurality of procedures and that endoscopes used in each procedure may be named with reference to the procedure, in each case the medical device, more aptly referred to as "videoscope", may include a handle, a flexible tube, a bending section and a camera operable to capture distal views.

A first aspect of the disclosure relates to an articulated tip part for an endoscope, comprising a bending section having a number of hingedly connected segments including a proximal end segment, a distal end segment, and a plurality of intermediate segments positioned between the proximal end segment and the distal end segment, wherein at least one of the end segments comprises a number of at least one depression or through-hole being provided in an outer circumferentially extending side wall of the respective end segment, a hardened adhesive adhering at least to a surface of another, separate member of the tip part and extending into the at least one depression or through-hole, so that the hardened adhesive in the at least one depression or through-hole forms a barb so as to secure the respective end segment to the other member of the tip part.

By providing a tip part in this way, an adhesive can be used to assemble the tip part, while it may not be required that the bending section is made of a material with relatively good adhesion properties. This is often the trade-off in material properties made by choosing a material with relatively good bending and manufacturability properties the material often has relatively poor adhesion properties. Often other parts of the tip part are not subject to the same material restrictions as the bending section and may be made of a material with relatively good adhesion properties. In this way, the bending section is secured to other parts of the tip part not by adhesion but by mechanically interlocking the bending section to other parts of the tip part. This may be a flexible and a cost-effective way of securing the bending section. However, it is not required that the bending section is made of a material with relatively poor adhesion properties. The provision of the at least one depression or through-hole may also increase the mechanical interlocking of a bending section and the other member when the bending section and the other member are made of materials with relatively good adhesion properties.

Additionally, the number of depressions or through-holes may be non-zero or at least 1, 2, 3, 4, 5, 6, 7, 8, 9, or 10.

The depressions or through-holes may be manufactured by removing material from the respective bending section or may be formed by moulding.

The hardened adhesive may or may not be present in a gap between the other, separate member of the tip part and the respective end segment. The hardened adhesive may be hardened by exposure to ultraviolet light.

Additionally or alternatively, the hardened adhesive may form an integral or continuous portion of hardened adhesive.

Additionally or alternatively, the hardened adhesive may be connected to the surface of the other member by adhesion and extend, potentially radially, from this surface into the at least one depression or through-hole of the bending section.

Additionally or alternatively, the barb of the hardened adhesive may secure or fixate the respective end segment to the other, separate member of the tip part potentially by preventing at least one type of relative movement from the group consisting of: translational, axial, radial, and/or rotational movement.

Additionally or alternatively, the depressions or through-holes may be provided at a proximal end of the proximal end segment and/or at a distal end of the distal end segment.

Additionally or alternatively, the shape of at least one, potentially all, of the depressions or through-holes may be selected from the group consisting of: circular, oval, square, triangular, pentagon, hexagon, polygon, or any other suitable shape.

The bending section may be a section allowing the tip part to bend relative to the insertion tube, potentially so as to allow an operator to manipulate the tip part, potentially by operating a control element of an operating handle, while inserted into a body cavity of a patient. Additionally or alternatively, the bending section may be integrally formed, potentially in one piece.

At least one hinge member may interconnect adjacent segments with each other, e.g. the proximal end segment with an adjacent intermediate segment and the distal end segment with an adjacent intermediate segment. Additionally or alternatively, each pair of adjacent segments may be interconnected by at least one, two, or three hinge members. The hinge member(s) may be bridging a gap between adjacent segments.

Each segment may comprise a proximal surface, potentially except the proximal end segment, facing a distal surface of an adjacent segment forming a gap therein between, and at least one hinge member may bridge the gap. Each segment may comprise a distal surface, potentially except the distal end segment, facing a proximal surface of an adjacent segment forming a gap therein between, and at least one hinge member may bridge the gap. The proximal surface and/or distal surface of each segment may be substantially planar.

Each segment of the bending section may be provided with a similar, potentially substantially equal, outer circumference, potentially around a central axis, which may potentially be a proximal-distal symmetry axis of the bending section. The segments may be substantially cylindrically and/or disc-shaped. Each segment may be substantially cylindrical disc-shaped with an outer circumferentially extending side wall, so that the tip part has a uniform outer contour. The outer circumferentially extending side wall may extend around a central axis, potentially a proximal-distal axis, of the tip part.

In this specification, the term "outer surface" or "exterior surface" may be understood as a surface facing toward a body cavity when the tip part is inserted into a body. However, the term "outer surface" or "exterior surface" shall not be construed as a surface necessarily capable of contacting the tissue of the patient, since another part or layer may be positioned between the outer or exterior surface and the tissue.

Additionally or alternatively, each hingedly interconnected segment may consist essentially of the same material and may be integrally formed, potentially in one piece.

Additionally or alternatively, the bending section may comprise or consist essentially of a polyolefin material, such as a plastic or elastomer material, with low surface energy. Low surface energy may in this specification be defined as a solid surface free energy (SFE) at 20° C. of less than 36, 35, 34, 33, 32, 31, 30, 29, 28, 27, 26, or 25 mN/m.

For the purposes of this specification, a material with good adhesion properties may be defined as a material with an SFE of more than 37, 38, 39, 40, 41, 42, 43, 44, or 45 mN/m.

For the purposes of this specification, a material with poor adhesion properties may be defined as a material with a solid surface free energy (SFE) at 20° C. of less than 45, 44, 43, 42, 41, 40, 39, 38, 37, 36, 35, 34, 33, 32, 31, 30, 29, 28, 27, 26, or 25 mN/m.

In this specification, the term "separate" may additionally or alternatively be defined as "non-continuous" or "non-integral".

In some embodiments, the other, separate member of the tip part may be a front end cap, or cap, which may be connected to the distal end segment.

In some embodiments, the other, separate member of the tip part may be a flexible tube, which may be connected to the proximal end segment.

The flexible tube may comprise an interior spacing defined by an outer circumferentially extending side wall. The side wall may be multi-layered. The outer circumferentially extending side wall may comprise an inner surface and/or an outer surface. The outer surface may be the surface of an outer-most layer and the inner surface may be the surface of an inner-most layer. The flexible tube may comprise a distal end, which may be connected to the proximal end segment of the bending section. The flexible tube may comprise a proximal end configured for connection with remaining parts of the endoscope, for instance an operating handle of the endoscope. The flexible tube may be integrally provided in one piece. The flexible tube may comprise or consist essentially of a polymeric material. The flexible tube may surround or enclose the cable passage and/or the working passage and/or the steering wire(s).

The flexible tube, the cap, and the bending section may be provided separately, and/or as separate components that are attached to each other. The flexible tube and the bending section may be formed as separate parts. The cap and the bending section may be formed as separate parts.

The bending section may comprise, potentially consist essentially of, a first material, and the flexible tube may comprise, potentially consist essentially of, a second, different material, and the cap may comprise, potentially consist essentially of, a third, different material. The flexible tube may be made of a polyolefin, potentially a plastic polymer. The cap may be made of a polyolefin, potentially a plastic polymer. The flexible tube and the cap may be made of different materials.

The bendable articulated tip part and/or the bending section and/or the cap and/or the flexible tube may form part of an insertion tube. The insertion tube or a distal end thereof may be suitable for insertion into a body cavity, potentially a lung, through a body opening, potentially a mouth. The body may be a natural and/or artificial body, potentially a human or animal body. The insertion tube may be connected to and extend from an operating handle towards a distal end of the endoscope. The tip part may be positioned at and form the distal end of the insertion tube.

A tubular sleeve, external sheath, or tubular bending cover may enclose the tip part and/or the flexible tube. The sleeve may seal the connection between the bending section and the flexible tube and may seal the connection between the bending section and the cap. The sleeve may provide the tip part and/or the flexible tube with an outer surface configured for insertion into a body cavity and contact with the patient's tissue, for instance a substantially smooth outer surface.

The tubular sleeve may be attached to the proximal end segment at a proximal end of the tubular sleeve, potentially by a hardened adhesive or laser welding, and/or to the distal end segment at a distal end of the tubular sleeve, potentially by a hardened adhesive or laser welding. The tubular sleeve may provide the tip part and/or the flexible tube with an outer surface configured for insertion into a body cavity, for instance a substantially smooth outer surface and/or an outer surface adapted for being in contact with tissue. The wall thickness of the tubular sleeve may be less than 0.3, 0.25, 0.2, 0.15, 0.1, 0.9, or 0.8 mm.

Additionally or alternatively, the tubular sleeve may be made of a polymeric material, such as polyurethane (PU) or thermoplastic polyurethane (TPU), e.g. Pellethane™ TPU. The tubular sleeve may be translucent or transparent, potentially to ultraviolet light.

Additionally, at least one segment chosen from the group consisting of the proximal end segment, the distal end segment, and the plurality of intermediate segments, and preferably at least some of the segments, may include a surface having an area profile with a two-dimensional, arithmetical mean height parameter, Sa, of at least 0.9 microns as measured using the International Organization for Standardization (ISO) standard "25178: Geometric Product Specifications (GPS)—Surface texture: areal" relating to the analysis of 3D areal surface texture as available on 5 Dec. 2018. The area profile forming the basis of this disclosure should be representative for a substantial area of the bending section, and should not contain surface defects or major discontinuities, for instance the area profile should not be located to span a gap between adjacent segments.

An advantage of such surface may be that covering at least the intermediate segments with the sleeve may be further facilitated because the sleeve may more easily be slid over the segments of the bending section. A typical way of assembling the tubular sleeve in the prior art is to apply a pressure differential, such as vacuum or an air blast, so as to increase the circumference of the tubular sleeve and thereby allow insertion of the bending section into the tubular sleeve, and thereafter reduce the pressure differential until the tubular sleeve wraps around the bending section to cover the intermediate segments. However, a lower pressure differential may be utilized or the tubular sleeve may even simply be manually slid over one of the end segments and onto the intermediate segments making the application of the pressure differential superfluous. This may provide the advantage of a simpler assembly process. Another advantage may be achieved when the tubular sleeve is positioned around the bending section, as the friction between the first area profile and the interior surface of the tubular sleeve is reduced. This further reduces the force required to manipulate the bending section and thus improves the manipulation of the tip part.

The plurality of intermediate segments may include a surface having a line profile with a one-dimensional, arithmetical mean height parameter, $R_a$, of at least 0.9 microns, the line profile being derived from an area profile of the surface as measured by the standard ISO 25178. Additionally, the line profile may be in a longitudinal direction, potentially a proximal-distal direction, of the tip part. Additionally, the one-dimensional, arithmetical mean height parameter, $R_a$, may have an identical range as the two-dimensional, arithmetical mean height parameter, $S_a$.

In some embodiments, the two-dimensional, arithmetical mean height parameter, Sa, of the area profile may be in the range of 1.8 microns to 4.5 microns as measured by the standard ISO 25178.

Additionally or alternatively, the one-dimensional, $R_a$, and/or two-dimensional, arithmetical mean height parameter, $S_a$, of the area profile may be 2.3±1.0 microns or in the range of 1.3 microns to 3.4 microns as measured by the standard ISO 25178.

In some embodiments, the two-dimensional, arithmetical mean height parameter, $S_a$, of the area profile may be 2340±520 nanometers or in the range of 1820 nanometers to 2860 nanometers as measured by the standard ISO 25178.

Additionally or alternatively, the two-dimensional, arithmetical mean height parameter, $S_a$, of the area profile may be at least 0.9, 1.0, 1.1, 1.2, 1.3, 1.4, 1.5, 1.6, 1.7, 1.8, 1.9, 2.0, 2.1, 2.2, or 2.3 microns and preferably be measured by the standard ISO 25178.

Additionally, the surface of the at least one segment may be an outer, circumferentially extending surface.

The two-dimensional, arithmetical mean height parameter, $S_a$, of the area profile may be calculated using the following formula in accordance with ISO 25168-3:

$$S_a = \frac{1}{A} \int \int_A |z(x, y)| \, dxdy$$

wherein A is the surface area of the area profile and |z(x,y)| is the height variation from the mean height plane of the area profile.

A number of line profiles may be derived from the area profile and a one-dimensional, arithmetical, mean height parameter, $R_a$, may be calculated using the following formula for each line profile derived from the area profile and averaging the result in addition to calculating the standard deviation:

$$R_a = \frac{1}{L} \int_L |z(x)| \, dx$$

wherein L is length of the line profile and |z(x)| is the height variation from the mean height plane of the line profile.

The tip part may comprise a camera assembly positioned at a distal end of the tip part and allowing an operator to inspect a body cavity, when the tip part is inserted into the body cavity. The camera assembly may be positioned in a spacing of the front end cap. The camera assembly may comprise one or some or all elements selected from the group consisting of: an image sensor configured to capture an image, at least one lens configured to alter light received by the image sensor, a camera housing for supporting the parts of the camera assembly, at least one light source configured to provide illumination for the image sensor, a printed circuit board, at least one signal cable for carrying an image signal from the camera assembly to the operator, and a power cable for supplying the camera assembly with electricity. The printed circuit board may be configured to process a signal from the image sensor. The signal cable and/or the power cable may be connected to printed circuit board. The signal cable may be configured for transmitting an image signal to the operating handle or an output for a monitor. The power cable may be configured to supply power to the printed circuit board.

The tip part or camera assembly may comprise at least one light source positioned at a distal end of the tip part so that light emitted from the light source is directed distally. At least one or all of the light source(s) may be light emitting diode(s) and/or light fibre(s). The light source(s) may be configured for providing illumination for the image sensor of the camera assembly. The number of light sources may be at least two or at the most two or exactly two.

The segments may comprise at least one cable passage for accommodating at least one cable, e.g. a signal cable for carrying an image signal and/or a power cable for carrying electricity. The cable passage may comprise a through-hole in each of the segments, potentially so as to form a cable passage, that may be extending from the distal end segment through the intermediate segment(s) to the proximal end segment. The cable passage may be positioned adjacent to a center of the segments. The tip part may comprise a signal cable for carrying an image signal and/or a power cable for carrying electricity, the signal and/or the power cable may be positioned in the cable passage.

The tip part may comprise a working passage. The working passage may be configured for accommodating a tube providing a working channel. The working passage may be different from the cable passage. The working channel may be a suction channel for providing a suction at the distal end of the tip part. The suction channel may be connected to a suction connector, potentially at a handle at the proximal end of the insertion tube. The working channel may allow insertion of surgical instruments there through to the distal end of the tip part. The working passage may be omitted to minimize the size of the tip part.

The tip part may comprise a steering wire. The steering wire may further be positioned in a steering wire passage of the tip part. The steering wire passage may be formed by a number of through-holes provided in the segments of the tip part. The steering wire passage may be different from the cable passage and/or the working passage. An end of the steering wire may be secured in the distal end of the tip part, and another end of the steering wire may be connected to a control element, potentially connected to a control lever of the control element. Thus by manipulating the control element the steering wire may be tensioned on one side of the plane of the hinge members, and slacked on the other, thus allowing the bending section to bend in a desired direction.

The steering wire may be a first steering wire and the articulated tip part may further comprise a second steering wire, potentially provided similarly to the first steering wire. The second steering wire may be positioned in a second steering wire passage.

In some embodiments, the tip part may further comprise a flexible tube, wherein the proximal end segment may comprise a first connection set including a number of depressions or through-holes, the first connection set being provided in an outer circumferentially extending side wall of the proximal end segment, a hardened adhesive mat adhere at least to a surface of the flexible tube of the tip part and extending into the first connection set, so that the hardened adhesive in the first connection set forms a barb so as to secure the proximal end segment to the flexible tube.

This may provide the advantage of a cost-effective and mechanically stable connection between the bending section and the flexible tube and/or cap.

The surface of the distal end of the flexible tube may be an internal or an outer surface of the flexible tube, potentially an internal or outer surface of a circumferentially extending side wall of the flexible tube.

Additionally or alternatively, the number of depressions or through-holes of the first connection set may be at least 1, 2, 3, 4, 5, 6, 7, 8, 9, or 10.

In some embodiments, the tip part may further comprise a cap, wherein the distal end segment may comprise a second connection set including a number of depressions or through-holes, the second connection set being provided in an outer circumferentially extending side wall of the distal end segment, a hardened adhesive may be adhering at least to a surface of the cap of the tip part and extending into the second connection set, so that the hardened adhesive in the second connection set forms a barb so as to secure the distal end segment to the cap.

Additionally or alternatively, the cap may have a proximal end positioned adjacent to the distal end segment. The cap may have a distal end, potentially forming the distal end of the tip part. The cap may comprise an outer circumferentially extending side wall, potentially enclosing a spacing. The cap may accommodate a camera assembly, potentially positioned in the spacing of the cap. The cap may comprise an end wall positioned at the distal end of the cap. The end wall may comprise a window, which may allow light to propagate there through to an image sensor of the camera assembly. The end wall may comprise an opening, potentially adjacent to the camera assembly, so that light passing through the opening is received by an image sensor of the camera assembly.

Additionally or alternatively, the number of depressions or through-holes of the second connection set may be at least 1, 2, 3, 4, 5, 6, 7, 8, 9, or 10.

In some embodiments, the hardened adhesive in the connection set may a positive engagement or connection to secure the respective end segment to the other member of the tip part, potentially preventing axial movement between the other member and the respective end segment.

Arranging the tip part in this way, may provide a more mechanically stable the tip part.

Additionally or alternatively, the hardened adhesive in the first connection set may form a positive engagement or connection to secure the proximal end segment to the flexible tube, potentially preventing axial movement between the flexible tube and the proximal end segment.

Additionally or alternatively, the hardened adhesive in the second connection set may form a positive engagement or connection to secure the distal end segment to the cap, potentially the barb of the second connection set preventing axial movement between the cap and the distal end segment.

In some embodiments, the other member of the tip part and the respective end segment may be positioned adjacently.

Arranging the tip part in this way, may provide a more cost-effective and mechanically stable the tip part.

Additionally or alternatively, the distal end of the flexible tube and the proximal end of the proximal end segment may be positioned adjacently.

Additionally or alternatively, a proximal end of the cap and the distal end of the distal end segment may be positioned adjacently.

In some embodiments, the other member of the tip part and the respective end segment may be positioned with an overlap, and the connection set may be in communication, potentially direct communication, with the overlap or is positioned adjacently to the overlap.

Additionally or alternatively, the distal end of the flexible tube and the proximal end of the proximal end segment may be positioned with an overlap, and the first connection set may be in communication, potentially direct communication, with the overlap or is positioned adjacently to the overlap.

Additionally or alternatively, the proximal end of the cap and the distal end of the distal end segment may be positioned with an overlap and the first connection set is in communication, potentially direct communication, with the overlap or is positioned adjacently to the overlap.

In some embodiments, the connection set may comprise at least one group of at least two depressions or through-holes being interconnected by a recess provided in the outer circumferentially extending side wall of the respective end segment, the hardened adhesive may be adhering at least to the surface of the other member of the tip part and extending from the surface into each respective group of depressions or through-holes of the connection set and into the recess interconnecting the respective group, thereby forming an anchor so as to secure the respective end segment to the other member of the tip part.

Additionally or alternatively, the recess may be a duct, channel, a cut-out, and/or a depressed portion of the outer circumferentially extending side wall of the respective end segment.

Additionally or alternatively, the recess may allow the adhesive to be positioned below an outer surface of the outer circumferentially extending side wall of the respective end segment. An outer surface of the hardened adhesive in the recess may be continuous with the outer surface of the outer circumferentially extending side wall of the respective end segment.

Additionally or alternatively, the first connection set may comprise at least one group of at least two depressions or through-holes being interconnected by a recess provided in the outer circumferentially extending side wall of the proximal end segment, the hardened adhesive adhering at least to a surface of the flexible tube and extending from the surface into the at least one group of depressions or through-holes of the first connection set and into the recess interconnecting the respective group, thereby forming an anchor so as to secure the proximal end segment to the flexible tube.

Additionally or alternatively, the second connection set may comprise at least one group of at least two depressions or through-holes being connected by a recess provided in the outer circumferentially extending side wall of the distal end segment, the hardened adhesive adhering at least to a surface of the cap and extending into the at least one group of depressions or through-holes of the second connection set and into the recess connecting the at least one group, thereby forming an anchor so as to secure the distal end segment to the cap.

In some embodiments, the number of intermediate segments may be at least 8, 9, 10, 11, 12, 13, 14, 15, 16, 17, 18, 19, 20, 21, 22, 23, 24, 25, 26, 27, 28, 29, or 30.

As the number of intermediate segments increases the material requirements does as well. By providing a tip part in this way, the number of intermediate segments can be increased while still allowing a simple, cost-effective and mechanically stable connection to other parts.

In some embodiments, the number of intermediate segments may be at least 11, at most 11, or exactly 11. In some embodiments, the number of intermediate segments may be at least 18, at most 18, or exactly 18. In some embodiments, the number of intermediate segments may be at most 8, 9, 10, 11, 12, 13, 14, 15, 16, 17, 18, 19, 20, 21, 22, 23, 24, 25, 26, 27, 28, 29, or 30. In some embodiments, the number of intermediate segments may be between 8-30, 9-28, or 10-26, 11-24, 12-22, or 13-20.

In some embodiments, the bending section may consist essentially of polyoxymethylene (POM) and the number of intermediate segments may be at least 8, 9, 10, 11, 12, 13, 14, 15, 16, 17, 18, 19, 20, 21, 22, 23, 24, 25, 26, 27, 28, 29, or 30. This may be a particularly advantageous material in combination with many intermediate segments.

In some embodiments, the respective end segment may enclose or surround, potentially completely enclose or surround, the other member of the tip part.

Additionally or alternatively, the respective end segment, potentially completely, encloses or surrounds a portion of the other member of the tip part.

Additionally or alternatively, the outer circumferentially extending side wall of the respective end segment encloses a spacing in which a portion of the other member of the tip part is positioned.

In some embodiments, the bending section may comprise, or consist essentially of, polypropylene (PP), polyethylene (PE), or polyoxymethylene (POM).

Providing a tip part of this type may provide the advantage that a bending section can be made of one or more of the above materials with relatively poor adhesion properties, while still allowing a simple, cost-effective, and mechanically stable connection.

Additionally or alternatively, the hingedly interconnected segments may comprise, or consist essentially of, polypropylene (PP), polyethylene (PE), or polyoxymethylene (POM).

Additionally or alternatively, the bending section may a portion of an outer layer of polypropylene (PP), polyethylene (PE), or polyoxymethylene (POM). The portion of the outer layer may be adjacent to the connection set.

Additionally or alternatively, a portion of the bending section adjacent to the connection set may consist essentially of polypropylene (PP), polyethylene (PE), or polyoxymethylene (POM).

In some embodiments, the at least one or both of the end segments may comprise at least one, two, three, or four centering ribs provided on an inner surface of the outer circumferentially extending side wall of the respective end segment, the centering ribs may be positioned to abut an outer surface of the other member of the tip part so as to center the other member of the tip part in the spacing of the respective end segment.

This may provide the advantage, that the other member of the tip part is substantially centered in the respective end segment, which may allow a hardened adhesive all around in a gap between the circumference of the other member and the adjacent circumference of the respective end segment. This may further improve interlocking properties of the barb of hardened adhesive as the risk of the other member abutting the respective end segment adjacent to a depression or through-hole, and thus reducing the interlocking of the barb, is reduced or even eliminated.

Additionally or alternatively, number of centering ribs may be at most 10, 9, 8, 7, 6, 5, 4, 3, 2, or 1.

Additionally or alternatively, the proximal end segment may comprise the at least one, two, three or four centering ribs being provided on an inner surface of the outer circumferentially extending side wall of the proximal end segment. The centering ribs may be positioned to abut an outer surface of the distal end of the flexible tube so as to center the distal end of the flexible tube in the spacing of the proximal end segment.

Additionally or alternatively, the number of depressions or through-holes of the connection set is spaced substantially equally from each other around the circumference of the respective end segment.

Additionally or alternatively, the number of depressions or through-hole of the first connection set may be spaced substantially equally from each other around the circumference of the proximal end segment.

Additionally or alternatively, the number of depressions or through-hole of the second connection set may be spaced substantially equally from each other around the circumference of the distal end segment.

In some embodiments of the tip part, the proximal end segment of the tip part is attached to a distal end of a flexible tube, the flexible tube further comprising an opposite, proximal end, wherein the at least one end segment is the proximal end segment of the bending section, the proximal end segment comprising a number of at least one depression or through-hole being provided in an outer circumferentially extending side wall of the proximal end segment, the hardened adhesive adhering at least to an outer surface of the flexible tube and extending into the at least one depression or through-hole, so that the hardened adhesive in the at least one depression or through-hole forms a barb so as to secure the proximal end segment to the flexible tube, and wherein the proximal end segment has at least three centering ribs on an inner surface of the outer side wall of the proximal end segment, the centering ribs being positioned to abut an outer surface of the distal end of the flexible tube so as to center the flexible tube in the spacing of the proximal end segment.

The tip part according to such embodiments may be denoted an endoscope or an endoscope part.

Alternatively or additionally, the proximal end segment has four centering ribs on an inner surface of the outer side wall of the proximal end segment, the centering ribs being positioned to abut an outer surface of the distal end of the flexible tube so as to center the flexible tube in the spacing of the proximal end segment.

Alternatively or additionally, the tip part, the flexible tube and the centering ribs extend in a longitudinal direction, potentially linearly in the longitudinal direction.

Alternatively or additionally, the at least one hole or depression includes at least two holes or depressions, and wherein at least one of the centering ribs in the longitudinal direction extends between two of the holes or depressions.

Alternatively or additionally, if three holes or depressions are provided, three centering ribs may extend in the longitudinal direction between sets of two respective of the holes or depressions, respectively, i.e. so that a centering rib extends between each set of two holes. Similarly, if four holes or depressions are provided, four centering ribs may extend in the longitudinal direction between sets of two respective of the holes or depressions, respectively. Similarly if five or more holes or depressions are provided.

Alternatively or additionally, each centering rib extends in a circumferential direction less than or equal to 10, 8, 5, or 3 percent of a total circumferential extent of the inner surface of the outer circumferentially extending side wall of the respective end segment.

Alternatively or additionally, each centering rib extends in a cross-sectional or radial direction less than or equal to 5, 4, 3, 2, or 1 percent of a maximum cross-sectional extent of the inner surface of the outer circumferentially extending side wall of the respective end segment.

Alternatively or additionally, the distal end of the flexible tube is inserted into a spacing of the proximal end segment of the bending section.

In some embodiments, at least one of, potentially all of, the number of depressions or through-holes of the connection set may have a non-sharp edge, preferably a rounded edge, bevelled edge, or chamfered edge.

This may provide the advantage of providing a better mechanical connection.

Additionally or alternatively, the non-sharp edge of the connection set is positioned at an inner side of the connection set or at an outer side of the connection set or at both sides of the connection set.

Additionally or alternatively, at least one of, potentially all of, the number of depressions or through-holes of the first connection set may have a non-sharp edge, preferably a rounded edge, bevelled edge, or chamfered edge.

Additionally or alternatively, at least one edge of, potentially all edges of, the number of depressions or through-holes of the second connection set may have a non-sharp edge, preferably a rounded edge, bevelled edge, or chamfered edge.

The rounded edge may have a round-radius of at least 0.01, 0.02, 0.03, 0.04, 0.05, 0.06, 0.07, 0.08, 0.09, or 0.10 mm, and potentially at most 0.5, 0.4, 0.3, 0.2, or 0.15 mm. A rounded edge with these dimensions has been shown to provide an increasingly strong connection.

In some embodiments, a bendable articulated tip part according to the first aspect may form part of a medical device, such as an endoscope.

The term "endoscope" may be defined as a device suitable for examination of natural and/or artificial body openings, e.g. for exploration of a lung cavity. Additionally, or alternatively, the term "endoscope" may be defined as a medical device. A specifically configured endoscope may take its name from the procedure for which it was designed. Example endoscopes include, therefore, colonoscopes, ear-nose-throat scopes, duodenoscopes, and gastro-intestinal scopes.

The endoscope may comprise a control element. The control element may be configured to allow an operator to control the steerable tip part of the insertion tube by the at least one steering wire. The control element may allow bending the articulated tip part in at least one direction, potentially in two directions, the two directions potentially being opposite. The control element may be accommodated in the operating handle. The control element may include a lever allowing an operator to control the control element. The lever may extend outwardly from the control element, potentially through the operating handle. The control element may be in the form of a roller or a roller disc.

The endoscope may comprise an operating handle. The operating handle may be suitable for allowing an operator to grip and to operate the endoscope, potentially with one hand. The operating handle may comprise a handle housing arranged at a proximal end of the insertion tube. The handle housing may accommodate the control element.

In some embodiments, a system for visually inspecting inaccessible places, such as human body cavities, is provided. The system comprises a video processing apparatus (VPA), such as an image monitor, and an endoscope with a tip part according to the first aspect of the disclosure, wherein the endoscope is connectable to the VPA, and an image display allows an operator to view an image captured by a camera assembly of the endoscope. The VPA may include the display screen or the display screen may be communicatively coupled to a VPA that does not include a display screen.

A second aspect of the disclosure relates to a method for securing a bending section to a flexible tube or a cap for at least partially assembling an articulated bendable tip part according to the first aspect of the disclosure. In some embodiments, the method comprises: a) providing a bending section comprising a number of hingedly connected segments including a proximal end segment, a distal end segment, and a plurality of intermediate segments positioned between the proximal end segment and the distal end segment, at least one of the end segments comprises a number of at least one depression or through-hole, the connection set being provided in an outer circumferentially extending side wall of the respective end segment; b) providing another member of the tip part separate from the bending section; c) injecting an adhesive into the at least one depression or through-hole and into contact with a surface of the other member of the tip part; and d) allowing or causing the adhesive to harden, whereby the hardened adhesive forms a barb at least adhering to the other member so as to secure the respective end segment to the other member of the tip part.

The step of injecting an adhesive may be performed by introducing a tube in a gap between the respective end segment and the other member or may be performed by injecting directly into the connection set.

The adhesive may be hardened by exposure to ultraviolet light. The step of causing the adhesive to harden may comprise exposing the adhesive to ultraviolet light.

The step c of the method may be performed after steps a and b, and step d of the method may be performed after step c.

Additionally or alternatively, the method may comprise a first group of steps and/or a second group of steps, wherein the first group, the proximal end segment comprising a first connection set including a number of depressions or through-holes being provided in an outer circumferentially extending side wall of the proximal end segment, and the first group comprises the steps of: providing a flexible tube separate from the bending section; injecting an adhesive into the first connection set and into contact with a surface of the flexible tube; and allowing or causing the adhesive to harden, whereby the hardened adhesive forms a barb so as to secure the proximal end segment to the flexible tube; wherein the second group, the distal end segment comprises a second connection set including a number of depressions or through-holes being provided in an outer circumferentially extending side wall of the distal end segment, and the second group comprises the steps of: providing a cap separate from the bending section; injecting an adhesive into the second connection set and into contact with a surface of cap; and allowing or causing the adhesive to harden, whereby the hardened adhesive forms a barb so as to secure the distal end segment to the cap.

In some embodiments, the method according to the second aspect of the disclosure further comprises a step of: positioning the respective end segment and the other member with an overlap, potentially so that the connection set is in communication with the overlap.

This may provide a particularly simple and cost-effective method of assembling the tip part since the adhesive may be injected directly into a connection set.

Additionally or alternatively, the method may comprise a step of inserting the other member into a spacing of the respective end segment.

Additionally or alternatively, the method may comprise a step of inserting the respective end segment into a spacing of the other member.

In some embodiments, the flexible tube may be inserted into the spacing of the proximal end segment and adhesive may be injected directly into the through-holes of the first connection set. The flexible tube that is provided may comprise a first section having a first radial cross-section area at a distal end thereof and a second section distal of the first section and having a second radial cross-section area smaller than the first radial cross-section area, the second section being inserted into the spacing of the proximal end segment. The second section may comprise an outer cylindrical surface. The first section radial cross-section area may also be larger than the second section radial cross-section area.

In some embodiments, the method may comprise reducing, prior to providing said flexible tube, an initial radial cross-section area of the second section to the second radial cross-section area. The initial radial cross-section area may equal the first radial cross-section area. The first section may comprise a tubular shape with a circular cross-section. The second section may comprise a tubular shape with a circular cross-section and a radius smaller than the radius of the circular cross-section of the first section.

Reducing a radial cross-section of the second section from the initial size to the second radial cross-section may comprise grinding an external surface of the second section from the initial size/cross-section to the second, reduced, radial cross-section. Belt or disk or wheel grinders may be used.

In addition to or alternatively to grinding, chemicals may be used to reduce the initial radial cross-section of the second section, for example by dipping. Furthermore, an escomatic lathe may be used to both reduce the second section and an intermediate section between the first section and the second section, providing two steps. Advantageously, the escomatic lathe permits use of a coil of tubing and cutting the tubing into discrete flexible tubes of a predetermined length while also cutting the intermediate and second sections to their desired radial cross-sections, e.g. external diameters.

A sleeve may be slid over the intermediate step and the bending section. The sleeve may be sealed at both ends to seal the bending section.

In some embodiments, the cap may be inserted into the spacing of the distal end segment and adhesive may be injected directly into the through-holes of the second connection set.

In some embodiments of the method, the at least one of the end segments is the proximal end segment, wherein the proximal end segment has at least three centering ribs on an inner surface of the outer side wall of the proximal end segment, and wherein the other member of the tip part is a flexible tube having a proximal end and a distal end, the method further comprising the step of inserting the distal end of the flexible tube into the proximal end segment, the centering ribs being positioned to abut an outer surface of the distal end of the flexible tube so as to center the flexible tube in the spacing of the proximal end segment, whereby the barb at least adheres to the flexible tube so as to secure the proximal end segment to the flexible tube. In an embodiment, a bendable articulated tip part for an endoscope comprises: a bending section having a number of hingedly connected segments including a proximal end segment, a distal end segment, and a plurality of intermediate segments positioned between the proximal end segment and the distal end segment, and a flexible tube comprising a proximal end and a distal end, wherein the proximal end segment of the bending section comprises a number of at least one depression or through-hole being provided in an outer circumferentially extending side wall of the proximal end segment, the side wall enclosing a spacing of the proximal end segment, a hardened adhesive adhering at least to an outer surface of the flexible tube and extending into the at least one depression or through-hole, so that the hardened adhesive in the at least one depression or through-hole forms a barb so as to secure the proximal end segment to the flexible tube, and wherein the proximal end segment has at least three centering ribs on an inner surface of the outer side wall of the proximal end segment, the centering ribs being positioned to abut an outer surface of the distal end of the flexible tube so as to center the flexible tube in the spacing of the proximal end segment.

The tip part according to this embodiment may be according to any one of embodiments of tip parts of this disclosure. The tip part according to this embodiment may be applied as the tip part of any one of the embodiments of endoscopes of this disclosure. The tip part according to this embodiment may be manufactured by the method according to any one of the embodiments of methods of this disclosure for manufacture of endoscopes.

A person skilled in the art will appreciate that any one or more of the above aspects of the disclosure and embodiments thereof may be combined with any one or more of the other aspects of the disclosure and embodiments thereof.

BRIEF DESCRIPTION OF DRAWINGS

The above-mentioned and other disclosed features, the manner of attaining them, and the advantages thereof will become more apparent and will be better understood by reference to the following description of disclosed embodiments taken in conjunction with the accompanying drawings, wherein:

FIG. 11a shows a side view of another embodiment of a tip part including the distal end of a flexible tube, FIG. 11b shows a cross-sectional view of the embodiment of the tip part along line E-E of FIG. 11a, FIGS. 12a, 12b and 12c show partial cross-sectional views of the distal end of the flexible tube of FIGS. 11a and 11b, FIG. 13a shows a side view of a further embodiment of a tip part including the distal end of a flexible tube, FIG. 13b shows a cross-sectional view of the embodiment of the tip part along line F-F of FIG. 13a, FIGS. 14a, 14b and 14c show partial cross-sectional views of the distal end of the flexible tube of FIGS. 13a and 13b, FIGS. 15a and 15b are perspective views of the bending section and front end cap of an embodiment of a medical device.

DETAILED DESCRIPTION

Figure 1A:
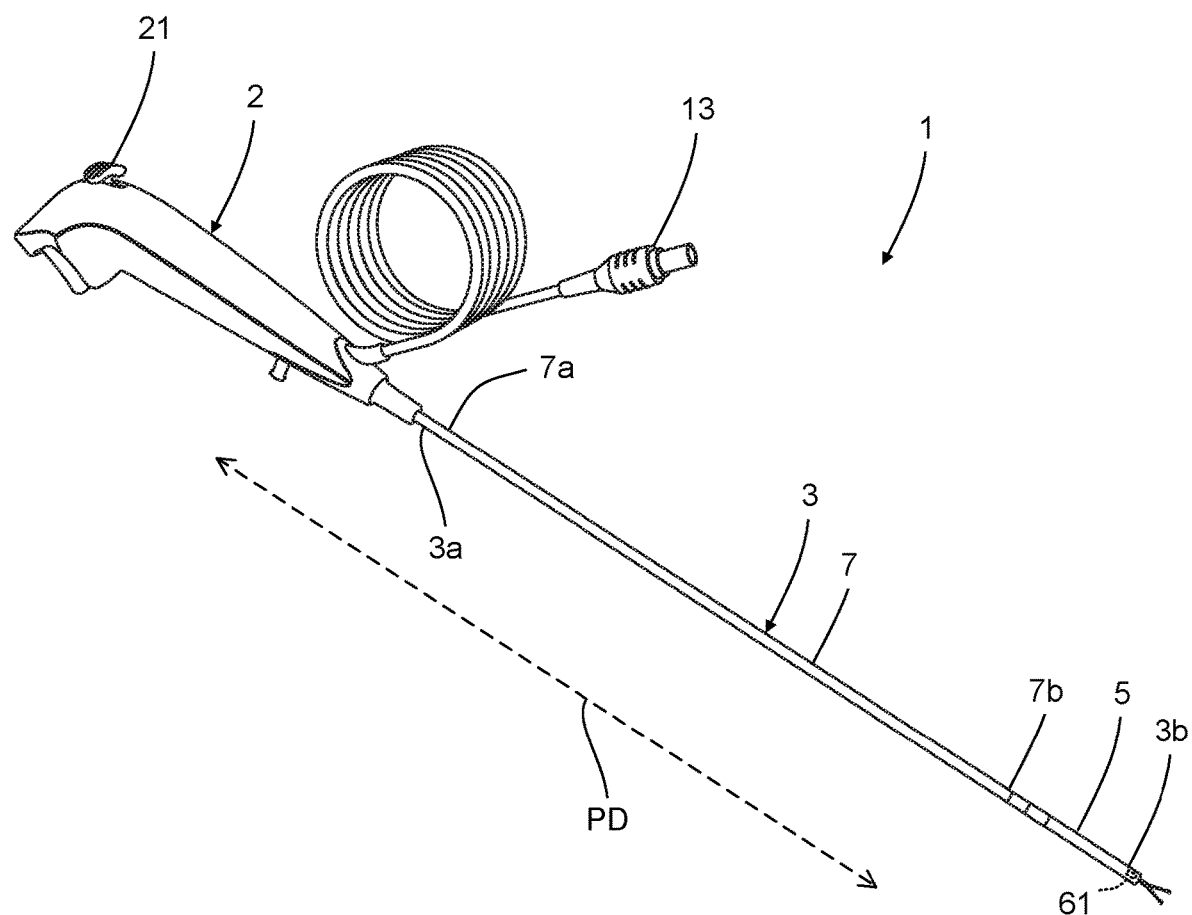
FIG. 1a shows a perspective view of an endoscope in which a tip part according to the first aspect of the disclosure is implemented.

Referring first to FIG. 1a, a medical device, illustratively an endoscope 1, is shown. The endoscope is disposable and, thus, not intended to be cleaned and reused. The endoscope 1 comprises an elongated insertion tube 3. At the proximal end 3a of the insertion tube 3 an operating handle 2 is arranged. The operating handle 2 has a control lever 21 for maneuvering an articulated tip part 5 at the distal end 3b of the insertion tube 3 by means of a steering wire (omitted for visualisation purposes). A camera assembly 61 is positioned in the tip part 5 and is configured to transmit an image signal through a cable 13 of the endoscope 1 to a VPA 11, exemplified as an image monitor.

VPA 11 may include a processor and memory having processing instructions stored therein and executable by the processor, the processing instructions operable to, when executed by the processor, receive image signals from the image sensor of the camera assembly, process the image signals, e.g. denoise and sharpen images, and output processed image signals operable to present images in an image display communicatively coupled to the VPA. A graphical user interface (GUI) module adapted to present a GUI with the image display may be provided, the GUI operable to, based on user commands, save images, save portions of video, and adjust processing parameters for the processor to change how the images are presented. The VPA may comprise an output port to communicatively couple the VPA with an image display. The VPA may also comprise a housing supporting an image display.

Figure 1B:
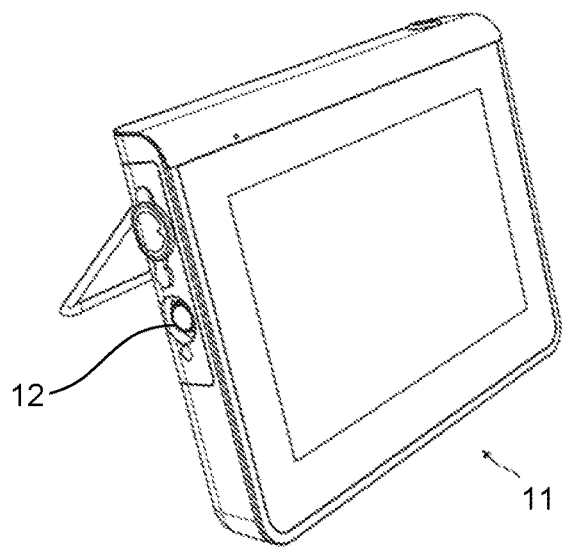
FIG. 1b shows a perspective view of a video processing apparatus to which the endoscope of FIG. 1a is connectable.

A system to inspect an internal cavity of a patient includes a medical device, of which an endoscope is an example thereof, and the VPA. In FIG. 1b, the VPA 11 is shown. The VPA 11 may allow an operator to view an image captured by the camera assembly of the endoscope 1. The VPA 11 comprises a cable socket 12 to which the monitor cable 13 of the endoscope 1 can be connected to establish a signal communication between the camera assembly 61 of the endoscope 1 and the VPA 11. Other medical devices include bronchoscopes, duodenoscopes, colonoscopes, ear and throat scopes, gastro-intestinal scopes and, generally, any medical device including an articulatable bending tip part with a camera assembly to generate images of the internal cavity. Bronchoscopes, duodenoscopes, colonoscopes, ear and throat scopes, and gastro-intestinal scopes are examples of endoscopes or, preferably, videoscopes.

Figure 2:
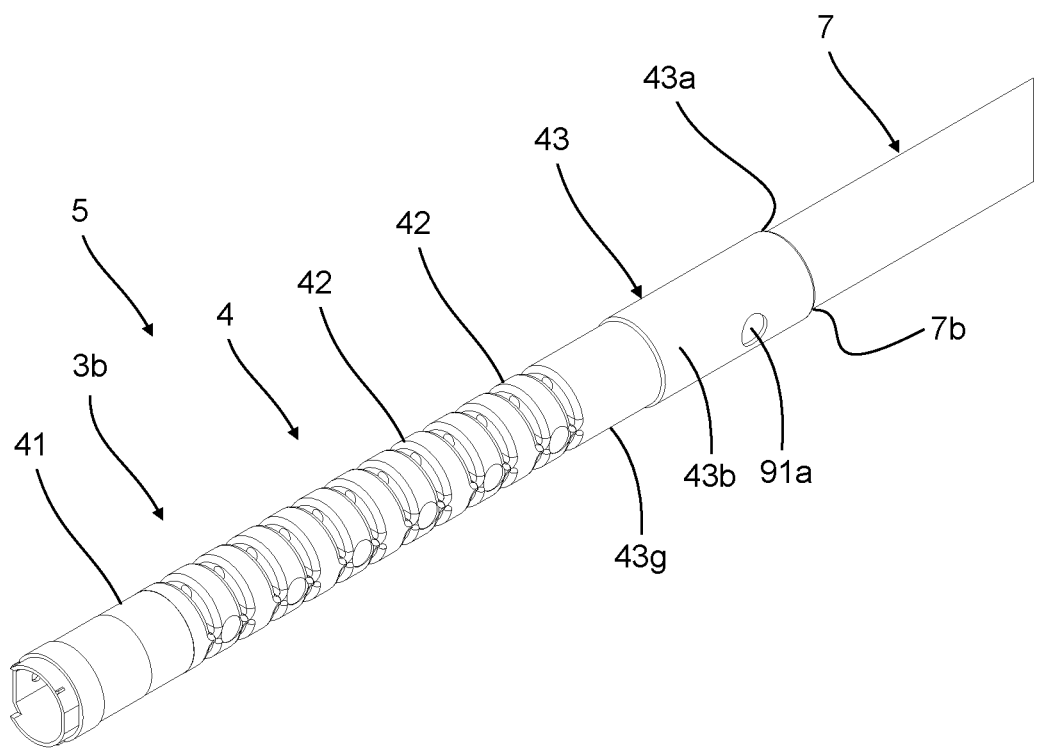
FIG. 2 shows a perspective view of a tip part according to a first embodiment, in which a hardened adhesive is omitted.
Figure 6:
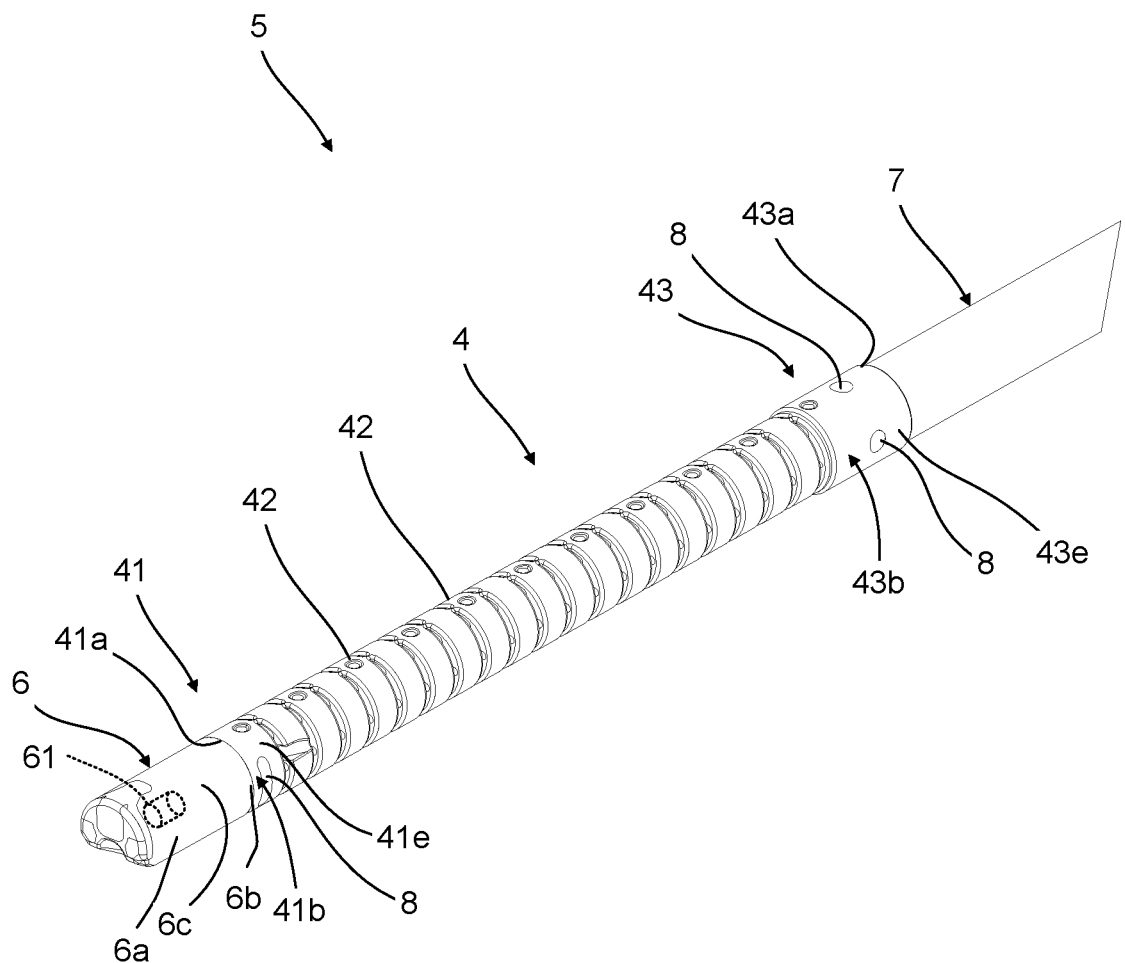
FIG. 6 shows a perspective view of a tip part according to a second embodiment.

Turning to FIG. 2, the distal end 3b of the insertion tube 3 is shown. In the figure shown, the camera assembly 61 and a cap (an example cap 6 is shown in FIG. 6), normally positioned at the very distal end of the insertion tube 3, are omitted. The insertion tube is suitable for insertion into a lung of a body through a mouth. The body can be a natural or artificial body, for instance a human or animal body. In this figure, the insertion tube 3 comprises a first embodiment of the tip part 5, which is articulated and bendable by operation of the control lever 21, and a flexible tube 7 attached to each other but provided as separate components before assembly thereof. The flexible tube 7 includes a distal end 7b connected to the tip part 5 and a proximal end 7a connected to the handle 2 of the endoscope 1.

The tip part 5 comprises a bending section 4 allowing the tip part 5 to bend relative to the flexible tube 7, so as to allow an operator to manipulate the tip part 5 while inserted into a body cavity. The bending section 4 comprises a plurality of hingedly interconnected segments including a distal end segment 41, a proximal end segment 43, and a number of intermediate segments 42 positioned between the proximal end segment 43 and the distal end segment 41. In the present embodiment, the number of intermediate segments 42 is eleven, but may in principle be less or even greater. Two hinge members of living hinge type interconnects adjacent segments with each other. The hinge members bridge a gap between adjacent segments. Each intermediate segment 42 is cylindrically disc-shaped with an outer circumferentially extending side wall, so that the bending section 4 has a substantially uniform outer diameter. A sleeve 100 (shown in FIG. 9b) or an external sheath may generally be provided to enclose the intermediate segments 42. The sleeve 100 or external sheath provides the bending section 4 with a smooth outer surface without gaps which is suitable for insertion into a body cavity.

Each of at least some of the segments may include an outer surface having an area profile with a two-dimensional arithmetical mean height parameter, Sa, of at least 0.9 microns, which may be referred to as a "textured" surface. The outer surfaces allow the sleeve 100 to slide thereon. Preferably the Sa is in the range of 0.9 microns to 9.0 microns as measured by standard ISO 25178. More preferably the Sa is in the range of 1.8 microns to 4.5 microns. Even more preferably the Sa is in the range of 1820 nanometers to 2860 nanometers. The textured surfaces may be provided in any of the bending sections disclosed herein. The textured surface may be provided in some, most, or all of the intermediate segments, and may also be provided in any surface that contacts the internal surface of the tubular sleeve during assembly. The textured surfaces may traverse an articulation plane to enable the tubular sleeve to slide. The articulation plane is the plane on which the bending section bends when articulated by the mechanism in the handle provided for that purpose.

A mold configured for molding the bending section may comprise a textured surface having an area profile with a two-dimensional, arithmetical mean height parameter, $S_a$, of at least 0.9 microns. The surface is internal and corresponds the outer surface of the bending section.

The bending section 4 and each hingedly interconnected segment 41, 42, 43 consist essentially of the same material and are integrally formed in one piece. The material is polypropylene (PP) but may be any suitable material, such as polyethylene (PE) or polyoxymethylene (POM). The flexible tube 7 consists essentially of a second, different, polymeric material from the bending section 4.

Figure 3:
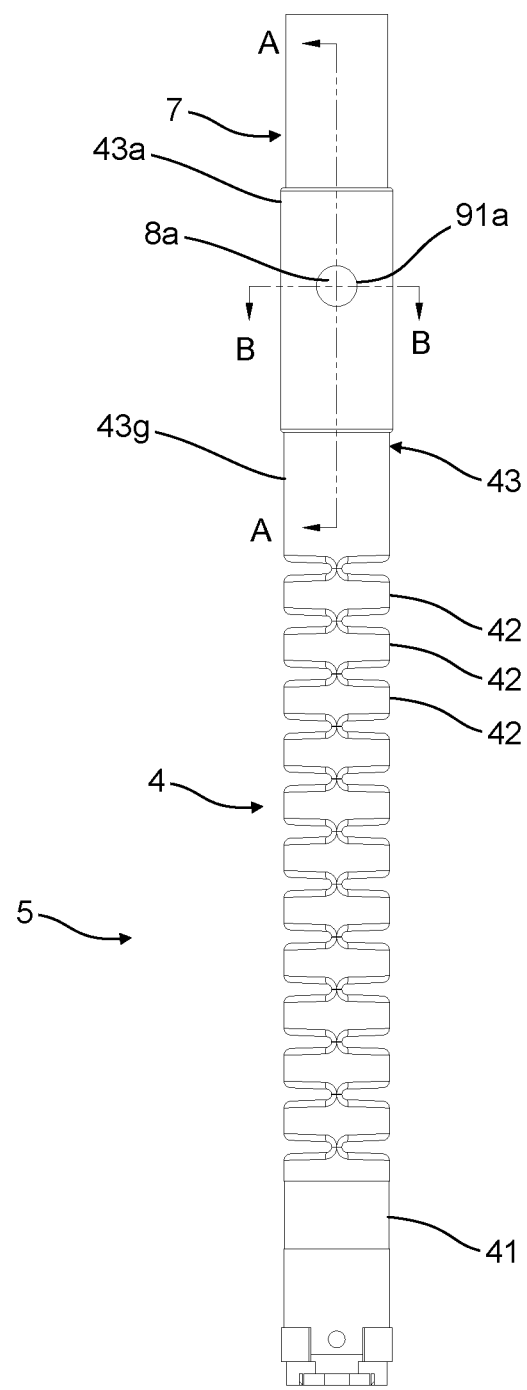
FIG. 3 shows a side view of the tip part of FIG. 2 in which a hardened adhesive is shown.

As seen in FIGS. 2 and 3, the proximal end segment 43 includes the proximal end 43a, a distal end 43g, and an outer circumferentially extending side wall 43b extending from the distal end 43g toward and including the proximal end 43a. The distal end 7b of the flexible tube 7 is positioned inside a space defined by an internal surface 43h of the side wall 43b to attach the flexible tube 7 to the bending section 4. Referring to FIGS. 11a-14c, in some variations the distal end 7b includes a second section 116 that is positioned inside the space defined by the side wall 43b. The side wall 43b has one or more cavities extending from the internal surface 43h. The cavities could be seen as part of the internal surface, however for clarity purposes the cavities are described as extending from the internal surface. In several examples the internal surface (except for the cavities and centering ribs) has a cylindrical shape, with the cavities extending radially outwardly therefrom and centering ribs extending radially inwardly therefrom. An adhesive 8 bonds to the outer surface of the distal end 7b of the flexible tube 7 and extends into the cavities to affix the proximal end segment 43 to the distal end 7b of the flexible tube 7.

Figure 4A:
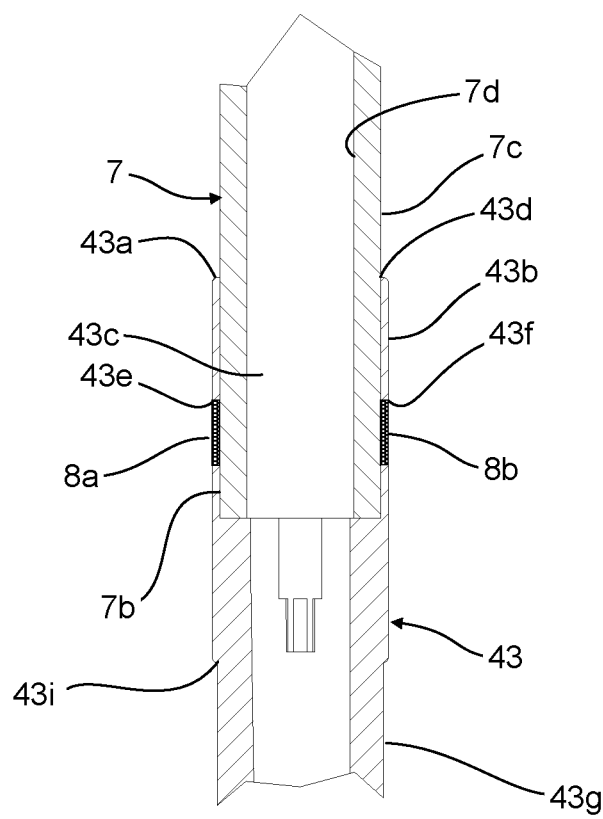
FIG. 4a shows a cross-sectional view of the tip part along line A-A of FIG. 3.
Figure 4B:
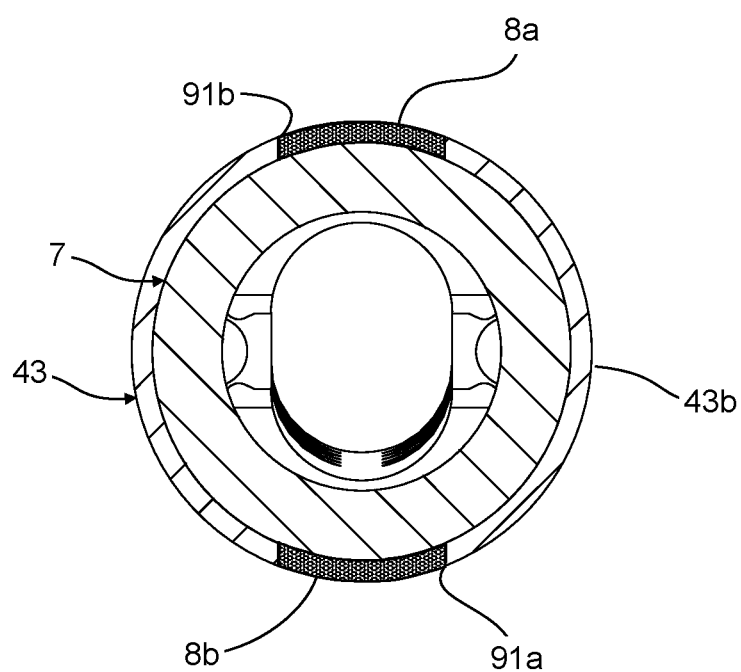
FIG. 4b shows a cross-sectional view of the tip part along line B-B of FIG. 3.

The cavities may comprise through-holes 91a, 91b, best seen in FIG. 4b. The proximal end segment 43 may be made from a polymer which is compatible with the adhesive 8 to form such a bond. The flexible tube 7 may be made, at least partly, from a different polymer or may comprise additives which cause the flexible tube to be less compatible with the adhesive 8 than the material from which the proximal end segment 43 is made. Therefore, once solidified, the adhesive 8 forms protrusions 8a, 8b which extend into the cavities, or through-holes 91a, 91b, and at least mechanically affix the proximal end segment 43 and the flexible tube 7. The protrusions 8a, 8b may be referred to as barbs.

Turning to FIGS. 4a and 4b, the outer circumferentially extending side wall 43b of the proximal end segment 43 encloses a spacing 43c with an opening 43d at a proximal end 43a of the proximal end segment 43. The distal end 7b of the flexible tube 7 has been inserted through the opening 43d, so that the distal end 7b of the flexible tube 7 is positioned overlapping the proximal end 43a of the proximal end segment 43 and in the spacing 43c of the proximal end segment 43. The proximal end segment 43 encloses and surrounds the distal end 7b of the flexible tube 7. The through-holes 91a, 91b connect surroundings with the spacing 43c of the proximal end segment 43. The circumferentially extending side wall 7a includes an inner surface 7d and an outer surface 7c, both being axially extending.

A first portion, or first protrusion, 8a of hardened adhesive 8 is adhered to the outer surface 7c of the flexible tube 7 at the distal end 7b thereof, and further extends into the first through-hole 91a. A second portion, or second protrusion, 8b of hardened adhesive 8 is adhered to the outer surface 7c of the flexible tube 7 at the distal end 7b thereof on an opposite side of the flexible tube 7, and further extends into the second through-hole 91b. Both the first 8a and second portion 8b are each continuous portions. In the present embodiment, the material of the proximal end segment 43 has relatively poor adhesion properties, thus the hardened adhesive 8 has greater adhesion to the outer surface 7c of the flexible tube 7 than to the proximal end segment 43. In other embodiments the materials for the flexible tube 7, the adhesive 8, and the proximal end segment 43 may be chosen to provide a stronger chemical bond in addition to the mechanical securement.

Each of the first portion 8a and second portion 8b of hardened adhesive 8 in the associated through-hole 91a, 91b forms a barb which secures or fixates the proximal end segment 43 to the distal end 7b of the flexible tube 7 by preventing relative movement between the proximal end segment 43 and the distal end 7b of the flexible tube 7. This prevention of relative movement includes preventing axial, radial, translational, and rotational movement. Additionally, the hardened adhesive may or may not be present in a gap between flexible tube 7 and proximal end segment 43. The first and section portions 8a, 8b of hardened adhesive form a positive engagement or connection between the distal end 7b of the flexible tube 7 and the proximal end segment 43.

In a variation of the present embodiment which is not shown in the drawings, the cavities are depressions formed in the inner surface 43h of the circumferentially extending side wall 43b of the proximal end segment 43 instead of or in addition to the through-holes 91a, 91b. In this embodiment, the adhesive 8 may be injected in the small gap between the inner surface 43h of the side wall 43b of the proximal end segment 43 and the outer surface 7c of the side wall 7a of the flexible tube 7. The adhesive may also be applied from the interior and through-holes provided in the flexible tube 7 for that purpose.

A proximal outer edge surface 43i is shown. A tubular sleeve 100 (shown in FIG. 11b) may be slid over the proximal end of the proximal end segment until it is adjacent to or abuts the proximal outer edge surface 43i, such that the proximal end of the tubular sleeve and the proximal end of the proximal end segment present a uniform outer surface, albeit with a small or no gap between the proximal outer edge surface and the tubular sleeve. No gap is shown in FIG. 11b.

Figure 5:
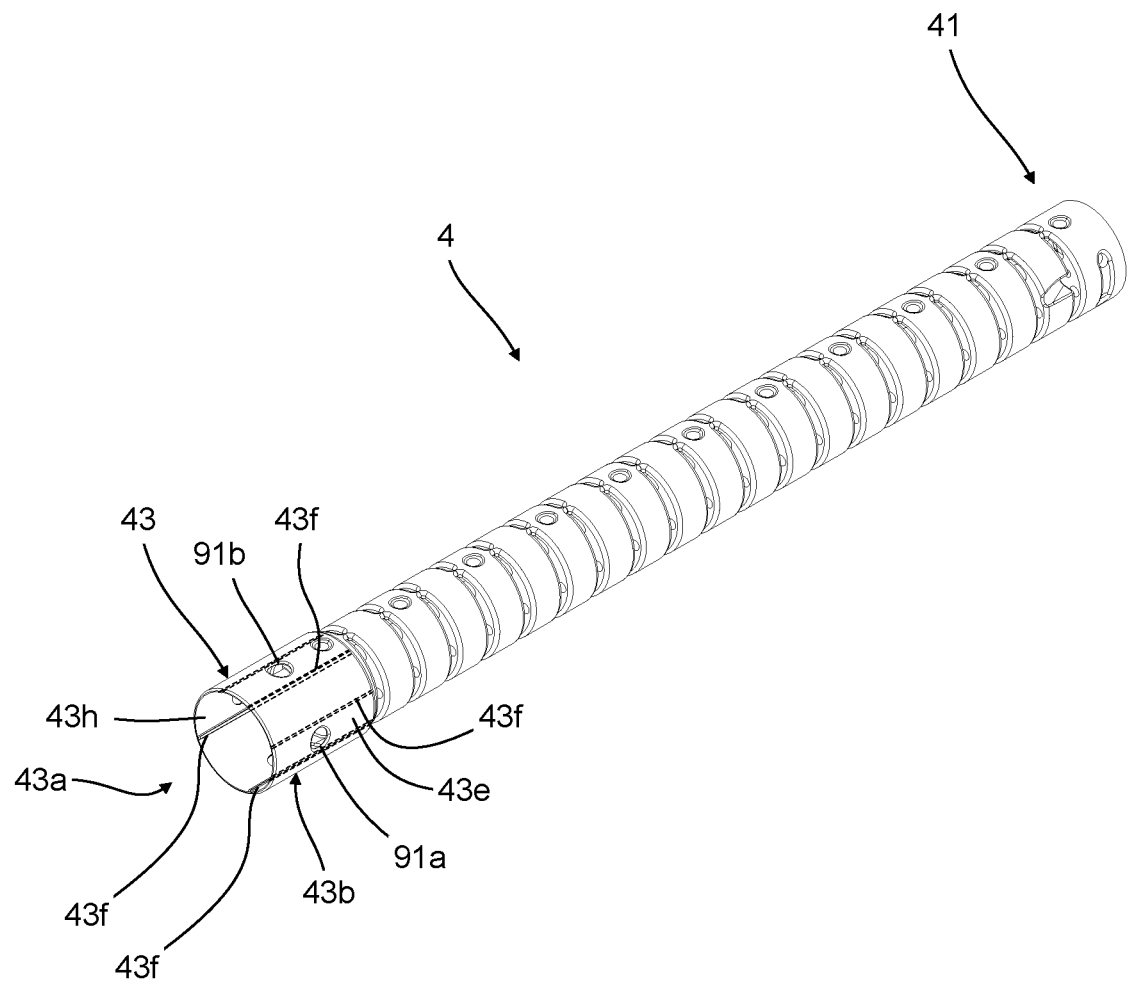
FIG. 5 shows a perspective view of a variation of the tip part of FIG. 2.

Turning to FIG. 5, in another variation of the present embodiment, the inner surface 43h of the side wall 43b of the proximal end segment 43 includes longitudinal protrusions provided to align or radially center the proximal end segment with the flexible tube 7. The flexible tube 7 may comprise corresponding indentations adapted to receive the longitudinal protrusions and thereby cause the flexible tube 7 to substantially radially align with the proximal end segment 43. Example longitudinal protrusions, or centering ribs, 43f are shown and are discussed with additional detail further below with reference to FIGS. 6, 7a and 7b. Although four longitudinal protrusions 43f are shown, more or less than four may be used. In the case where corresponding longitudinal indentations are provided, protrusions which are not necessarily long may be used, such as guiding stubs that slide in the longitudinal indentations during assembly to prevent rotation of the flexible tube 7 within the proximal end segment 43. As seen in FIG. 5, the centering ribs are circumferentially spaced at 90 degree intervals, deemed evenly distributed along the inner surface of the side wall. More or less centering ribs may be used, and the circumferential spacing may be adjusted accordingly. Of course the centering ribs do not need to be evenly distributed so long as the effect of their distribution is to center the proximal end segment or whatever member is to be inserted in a side wall having such protrusions.

In another embodiment which is not shown in the drawings, the flexible tube 7 is positioned exteriorly on the proximal end segment 43, so that the distal end 7b of the flexible tube 7 encloses and surrounds the proximal end segment 43. In this embodiment, the adhesive may be applied from the interior of the proximal end segment 43 or flexible tube 7. The flexible tube 7 may include a circumferential side wall, similar to the proximal end 43a of the proximal end segment 43, defining a spacing that receives the proximal end 43a, and of course the proximal end segment 43 would in such case omit the circumferential side wall.

In the following, a method of attaching the flexible tube 7 to the proximal end segment 43 is described. The method comprises: providing the bending section 4 and the flexible tube 7 as separate components; positioning a distal end 7b of the flexible tube 7 adjacent to the through-holes 91a, 91b provided in the outer circumferentially extending side wall 43b of the proximal end segment 43 of the bending section 4 so that the through-hole 91a, 91b and the distal end 7b of the flexible tube 7 are overlapping; injecting a first portion 8a and a second portion 8b of adhesive 8 into and filling up the associated through-holes 91a, 91b so that the first portion 8a and second portion 8b of the adhesive 8 are in contact with the outer surface 7c of the distal end 7b of the flexible tube 7; and allowing or causing the adhesive 8 to harden forming a barb so as to secure or fixate the bendable articulated tip part 5 to the flexible tube 7 by forming a positive engagement or a positive connection between the bending section 4 and the flexible tube 7.

Figure 7A:
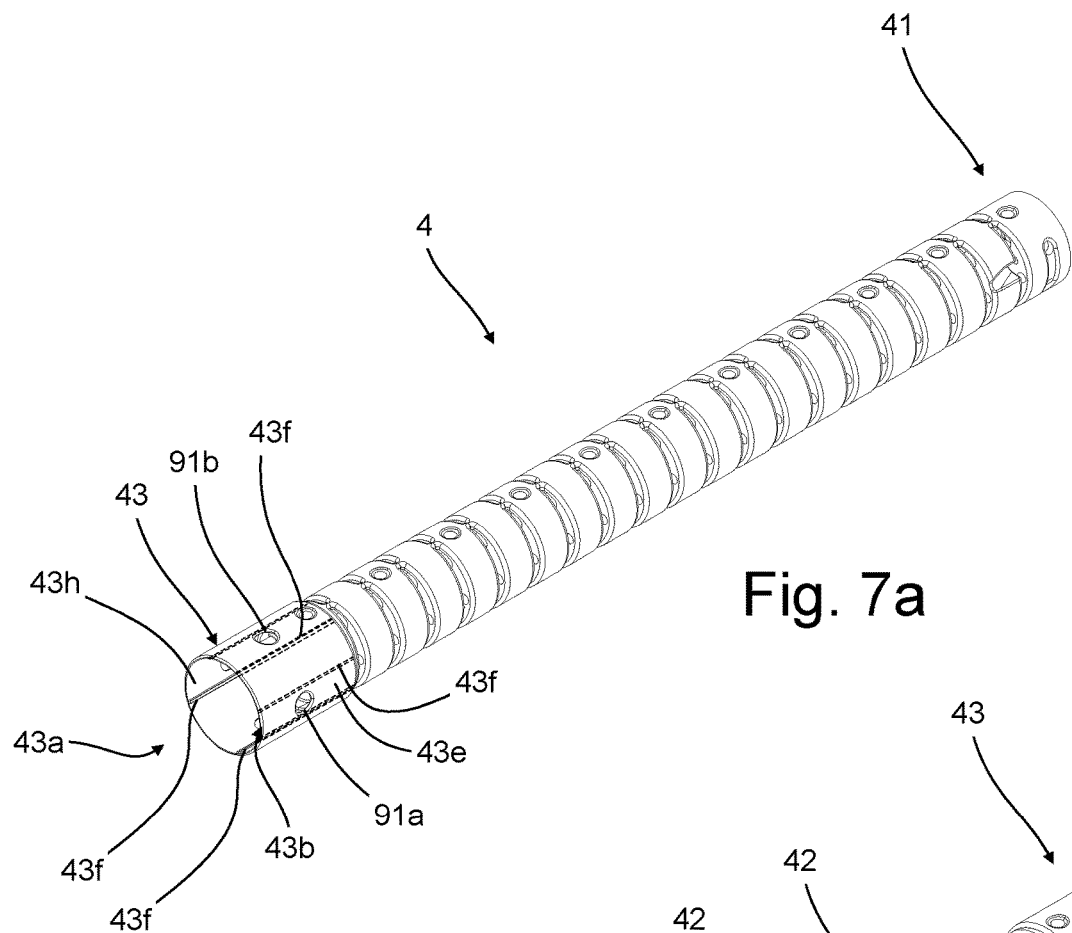
FIGS. 7a and 7b show a perspective view of the bending section of the tip part of FIG. 6 in which the hardened adhesive is omitted.
Figure 7B:
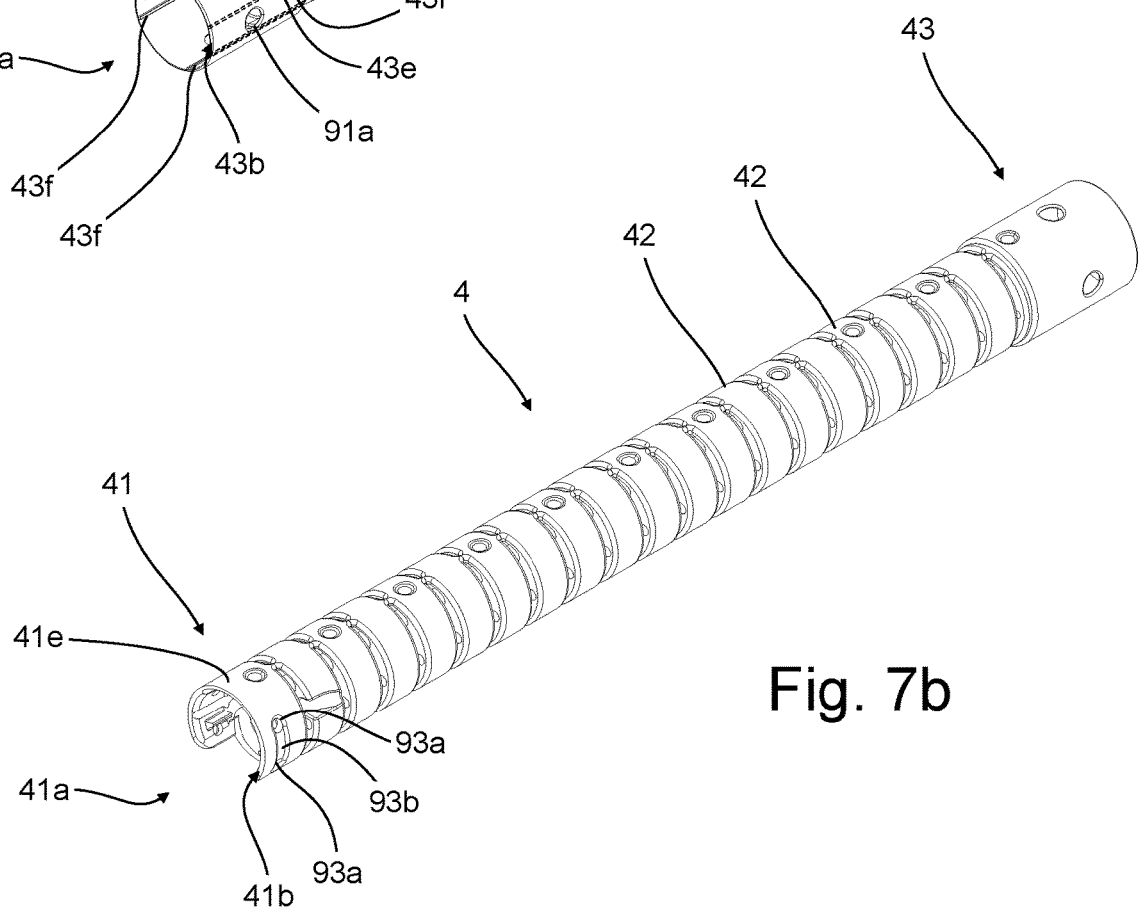

Referring to FIGS. 6, 7a and 7b, a second embodiment of the tip part 5 is shown. In this second embodiment, the tip part 5 comprises a bending section 4, a cap 6, and a flexible tube 7. The bending section 4 comprises a plurality of hingedly interconnected segments including a distal end segment 41, a proximal end segment 43, and a number of intermediate segments 42 positioned between the proximal end segment 43 and the distal end segment 41. In the present embodiment, the number of intermediate segments 42 is 18, but may in principle be less or even greater. The bending section 4 is formed in one piece of polyoxymethylene (POM). The proximal end segment 43 is attached to the distal end 7b of the flexible tube 7. The distal end segment 41 is attached to the proximal end of 6b of the cap 6. Three hinge members of living hinge type interconnects adjacent segments with each other. The hinge members bridge a gap between adjacent segments. The second embodiment is similar to the first embodiment; however, the differences are described below.

As described above with reference to FIG. 5, the proximal end segment 43 may further comprise centering ribs 43f provided on the inner surface 43h of the outer circumferentially extending side wall 43b of the proximal end segment 43. The centering ribs 43f are positioned to abut the outer surface 7c of the distal end 7b of the flexible tube 7 so as to center the distal end 7b of the flexible tube 7 in the spacing 43c of the proximal end segment 43 as best seen in FIG. 8b.

The tip part 5, the flexible tube 7 and the four centering ribs 43f extend linearly in the longitudinal direction, which extends from the distal end 3b towards the proximal end 3a. Each of the centering ribs 43f may extend in the longitudinal direction from the opening 43d between and beyond two respective holes 91a to 91d. Holes 91a to 91d are best seen in FIGS. 7a, 7b, 8a, 8b, and 9b. As also seen in FIG. 9b, each centering rib 43f may extend in a circumferential direction less than or equal to 10 percent of a total circumference, visible in FIG. 9b, of the inner surface 43h of the outer circumferentially extending side wall of the proximal end segment 43. Each centering rib 43f further extends in a cross-sectional or radial direction, i.e. in a direction of a diameter of the inner surface 43g as shown in FIG. 9b, less than or equal to 5 percent of a maximum cross-sectional extent, i.e. the diameter, of the inner surface 43h.

FIG. 6 shows the cap 6 having a circumferentially extending side wall 6a and a proximal end 6b. The camera assembly 61 is disposed within the cap 6, which is mounted onto the distal end segment 41. Attachment features of the cap 6 and the distal end segment 41 will be described with reference to FIGS. 7b, 8b, and 9. FIG. 8b is an expanded view of FIG. 8a, both views showing cross-section lines C-C and D-D, with corresponding cross-sectional views shown in FIGS. 9a (distal end) and 9b (proximal end).

Figure 8A:
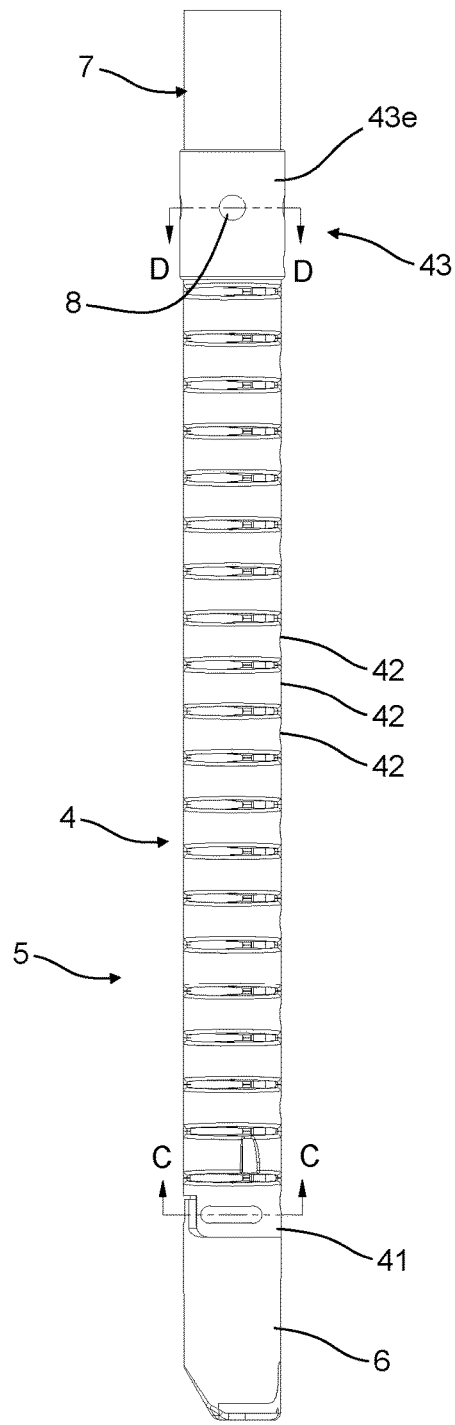
FIG. 8a shows a side view of the tip part of FIG. 6.
Figure 8B:
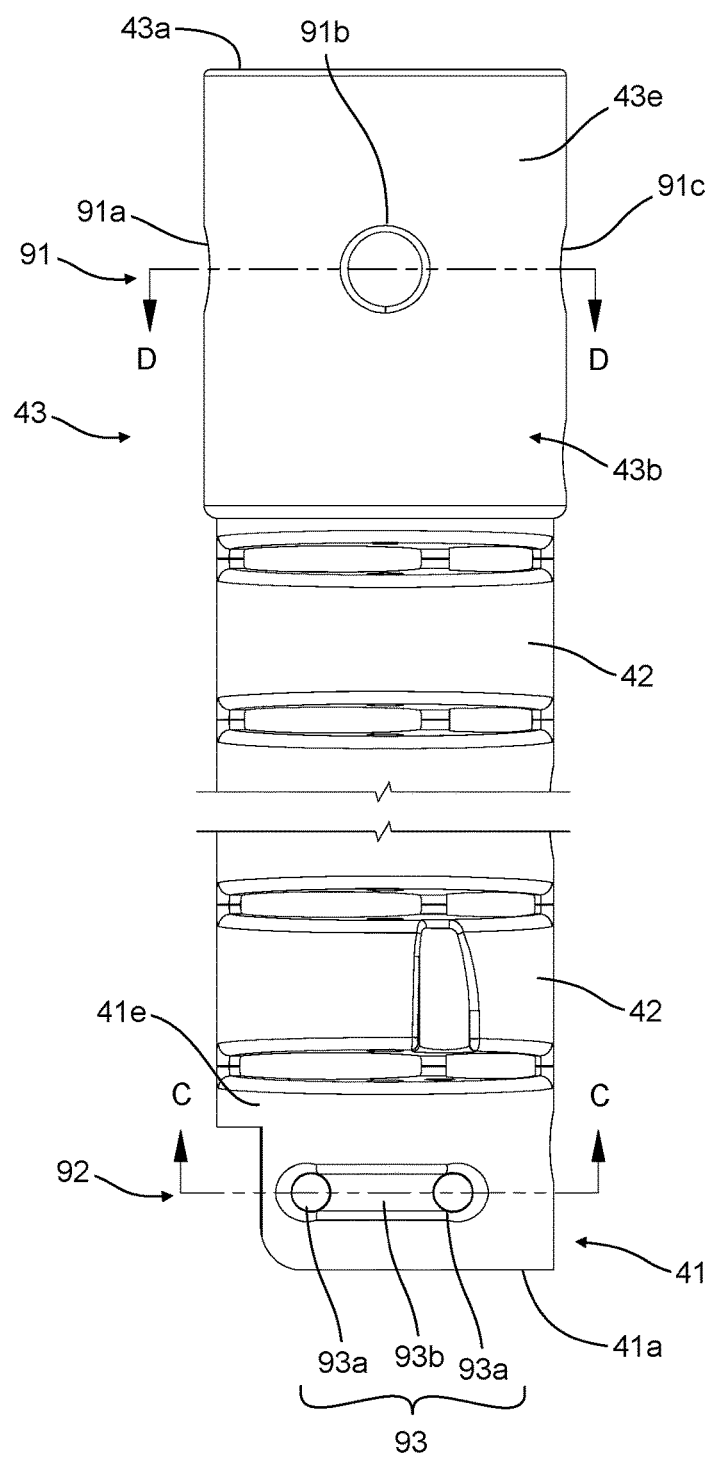
FIG. 8b shows a close-up side view of the bending section of FIG. 8a, in which some intermediate segments, other parts of the tip part and the adhesive are omitted.

Referring to FIG. 8b, the distal end segment 41 comprises a second connection set 92 including two groups 93, 94 each having two through-holes 93a, 94a and a recess 93b, 94b interconnecting the two through-holes of each group 93, 94. The through-holes of the second connection set 92 are provided in an outer surface 41e of the outer circumferentially extending side wall 41b of the distal end segment 41. The recesses 93b, 94b are provided in the outer surface 41e of the outer circumferentially extending side wall 41b of the distal end segment 41. In another embodiment which is not shown in the drawings, the distal end of the distal end segment 41 is positioned within a side wall extending from the cap.

Figure 9A:
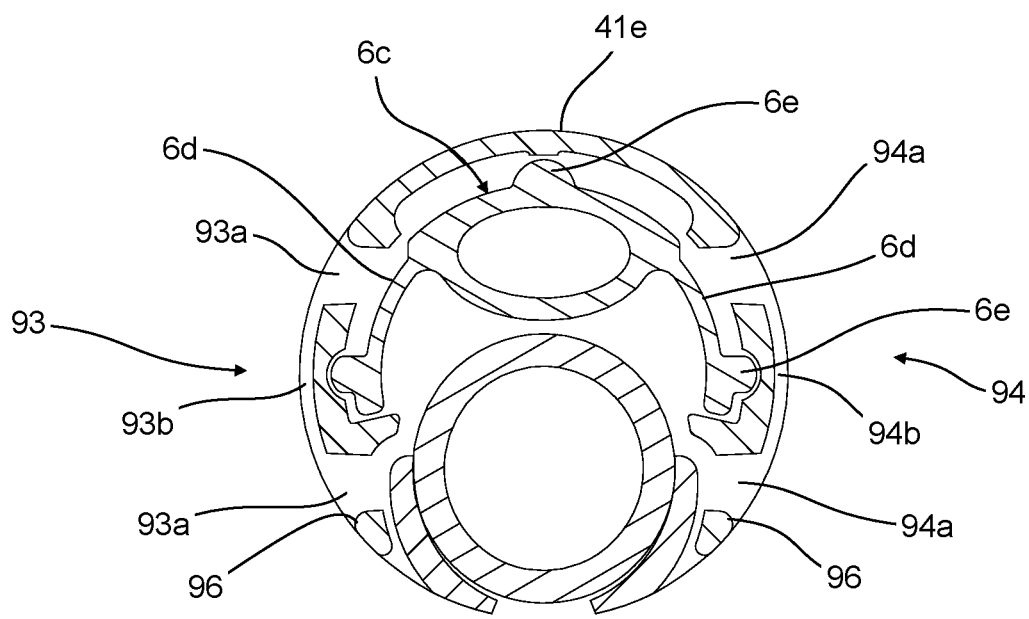
FIG. 9a shows a cross-sectional slice view of the tip part along line C-C of FIG. 8a, FIG. 9b shows a cross-sectional slice view of the tip part along line D-D of FIG. 8a, FIG. 10 shows an expanded view of a section of FIG. 9b.
Figure 9B:
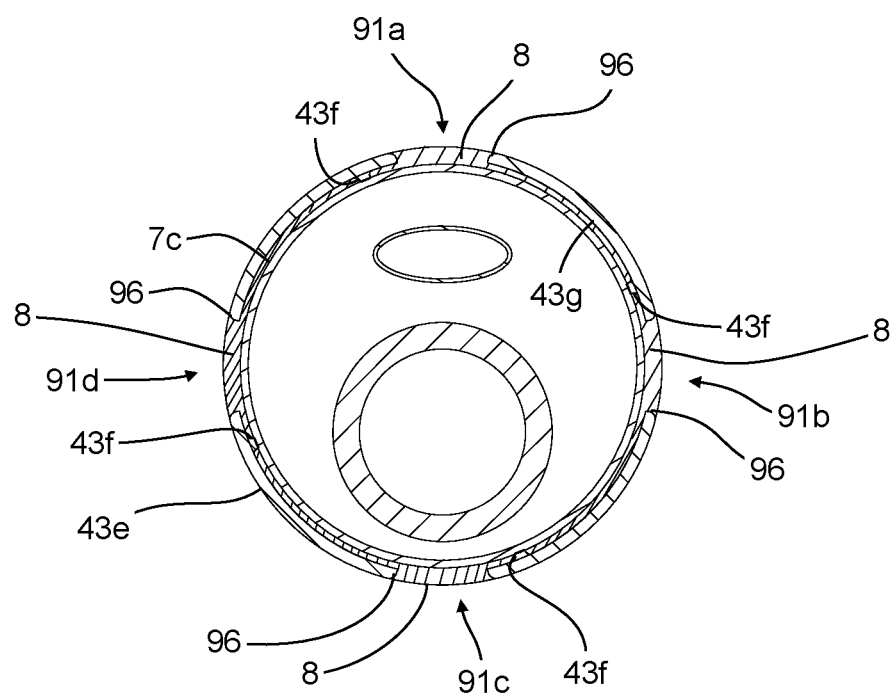

Referring now to FIG. 9a, the cap 6 may comprise a proximal cap end 6c extending from the circumferential side wall 6a and having a surface 6d. The proximal cap end 6c projects into the distal end segment 41 when assembled. Radial protrusions 6e may extend radially from the surface 6d and contact the internal surface of the side wall 41b to center the cap 6 in the distal end segment 41 and provide space for adhesive 8 to distribute evenly between them. The adhesive 8 adheres to the surface 6c of the cap 6 and extends into the second connection set 92. In this way the hardened adhesive 8 forms a barb in the second connection set so as to secure the distal end segment 41 to the cap 6. The hardened adhesive 8 forms an integral portion in each of the groups 93, 94 of the second connection set 92.

Figure 10:
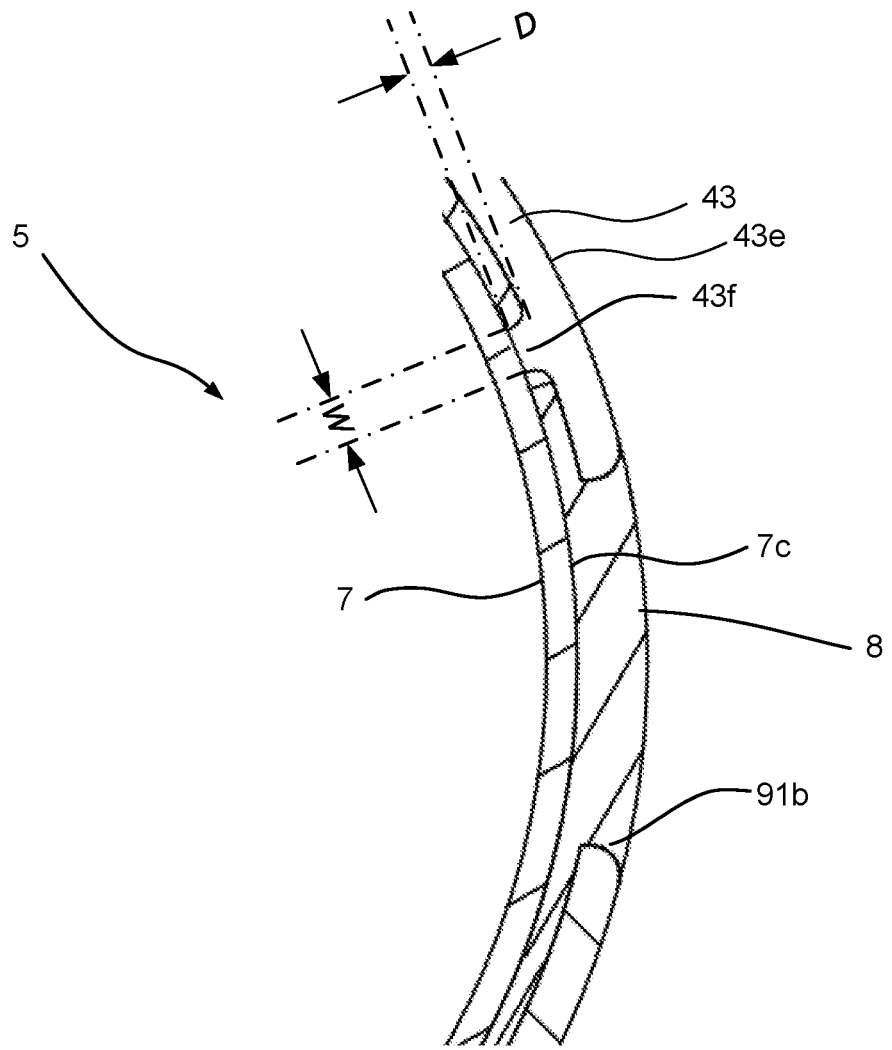

Returning to FIG. 8b, the proximal end segment 43 comprises a first connection set 91 including four through-holes 91a, 91b, 91c, 91d. The through-holes of the first connection set 91 are provided in the outer surface 43e of the outer circumferentially extending side wall 43b of the proximal end segment 43. FIGS. 9b and 10 illustrate that the hardened adhesive 8 adheres to the outer surface 7c of the flexible tube 7 and extends into the first connection set 91.

FIG. 10 shows an expanded section of FIG. 9b, to illustrate one example of the relationship between the width, W, and radial length, or depth D, of the centering ribs 43f relative to the flexible tube circumference. The inner surface has an inner perimeter, wherein each of the centering ribs has a width W measured perpendicularly to a longitudinal direction and a depth, D, measured radially from the inner surface, and wherein the width of each centering rib is less than or equal to 10 percent of the inner perimeter. The depth of each of the centering ribs may be less than the width. A cross-section of the internal space of the peripheral wall taken perpendicularly to the longitudinal direction has a maximum cross-sectional extent. If the cross-section is circular, the maximum cross-sectional extent is the diameter of the circle. If the cross-section is oval, the maximum cross-sectional extent is the length of the major axis. The depth of each of the centering ribs may be less than or equal to 5 percent of the maximum cross-sectional extent. The internal surface may have a substantially tubular shape having a diameter, wherein the depth of each of the centering ribs is less than or equal to 5 percent of the diameter.

As seen in FIGS. 8b and 9b, every through-hole of each connection set 91, 92 has a rounded edge 96 at the interface between the through-hole and the outer surface 41e, 43e of the respective end segment 41, 43 all around the circumference of each through-hole.

In the following, a method of attaching the flexible tube 7 and the cap 6 to the bending section 4 as shown in FIGS. 7a and 7b to obtain a tip part 5 is described. The method comprises the sequential steps of: providing a bending section 4 comprising a number of hingedly connected segments including a proximal end segment 43, a distal end segment 41, and a plurality of intermediate segments 42 positioned between the proximal end segment 43 and the distal end segment 41. The proximal segment 43 comprises a first connection set 91 with four through-holes 91a, 91b, 91c, 91d provided in an outer surface 43e of outer circumferentially extending side wall 43b of the proximal end segment 43. The distal end segment 41 comprises a second connection set 92 with two groups 93, 94 of two through-holes 93a, 94a each provided in an outer surface 41e of outer circumferentially extending side wall 41b of the distal end segment 41, the through-holes 93a, 94a of each group 93, 94 are interconnected by a recess 93b, 94b provided in the outer circumferentially extending side wall 41b; providing a cap 6 and a flexible tube 7, both as separate components from the bending section 4; inserting the distal end of the flexible tube 7 into the proximal end of the proximal end segment 43 to form an overlap, so that the first connection set 91 is in communication with the overlap; positioning the distal end of the distal end segment 41 and proximal end of the cap 6 with an overlap, so that the second connection set 92 is in communication with the overlap; injecting, from the outside, an adhesive 8 into and filling the first and second connection set 91, 92 and into contact with, respectively, an outer surface of the flexible tube 7 and a surface 6c of the cap; and allowing or causing the adhesive to harden, whereby the hardened adhesive 8 in the first connection set 91 forms four barbs adhering to the flexible tube 7 so as to secure the proximal end segment 43 to the flexible tube 7, and whereby the hardened adhesive 8 in the second connection set 92 forms two four barbs and two anchors adhering to the cap so as to secure the distal end segment 41 to the cap 6.

In a variation of the present embodiment, the method further comprises reducing a periphery of the flexible tube from a first radial cross-section area at a distal end thereof to form a second section with a second, smaller, periphery and radial cross-section area, forming a first step therebetween, and inserting the second section into the spacing in the proximal end segment of the bending section. Thereafter, injecting the adhesive to attach the outer surface of the second section of the flexible tube and the inner surface of the proximal end segment of the bending section. An apparatus to exemplify an embodiment of a method of reducing the first periphery is described with reference to FIGS. 16a and 16b. Examples of embodiments of flexible tubes with second sections are described with reference to FIGS. 11a-14c. In other respects, flexible tubes 110 and 120 are the same as the embodiments of flexible tube 7 described above. Reducing the periphery may comprise reducing the radial cross-section of the flexible tube. The second section may be contiguous to the first section or spaced apart by an intermediate section that is contiguous to the first section and to the second section.

The second section may be inserted until the first step abuts the proximal end of the proximal end segment of the bending section.

The first periphery, or outer surface of the first section, may be flush with the outer surface of the proximal end of the bending section.

In one example, the method further comprises: reducing a periphery of the flexible tube to form an intermediate section with an intermediate, smaller, periphery and radial cross-section area, forming a second step therebetween, the intermediate section having a radial cross-section area larger than the second section. After injecting the adhesive to attach the outer surface of the second section of the flexible tube and the proximal end segment of the bending section, the method further comprises sliding a sleeve over the bending section and the intermediate section of the flexible tube.

The second section may be inserted until the first step abuts the proximal end of the proximal end segment of the bending section, and the sleeve may be slid until it abuts the second or intermediate step.

The outer surface of the sleeve may be substantially flush with the outer surface of the first section of the flexible tube and the outer surface of the intermediate section may be substantially flush with the outer surface of the proximal end segment of the bending section. The sleeve may, thereby, seal from the distal end of the flexible tube to the distal end segment. The sleeve may be adhesively bonded to the first section or the intermediate section of the flexible tube and to the distal end segment of the bending section or to the end cap.

Turning to FIGS. 11a, 11b, and 12a-c, the flexible tube 7 is depicted as flexible tube 110 to illustrate variations of the foregoing embodiments. The flexible tubes 7, 110, and 120 (described with reference to FIGS. 13a-14c) may comprise a multi-layer structure The circumferentially extending side wall 7a comprises an inner layer, depicted as an inner tube 122 having inner surface 7d, an intermediate layer, depicted as an intermediate tube 124, and an outer layer, depicted as an outer tube 126 having outer surface 7c. The inner tube 122 may comprise a coil. In one example, the coil is a metal coil that provides the flexible tube structural integrity and flexibility to bend. The intermediate tube 124 may comprise a sheath or braid surrounding the inner tube. The outer tube 126 may comprise a polymer which is extruded over the intermediate tube 124 or over the inner tube 122 if the intermediate tube 124 is omitted. The polymer may penetrate into the intermediate tube and/or the inner tube. Flexible tubes with such multi-layer structures are known. The diameter of the outer tube, or outer layer, 126 is reduced to form the second section and the intermediate section. The diameter of the second section is, preferrably, larger than the diameter of the intermediate tube, or layer, 124, thereby providing a polymeric bonding surface to bond to the bending section.

The outer tube 126 may be comprised of various polymers. An example polymer is polyurethane, which is relatively soft, typically ranging between Shore A 80-90 depending on the clinical use. For example, a gastroscope may use a Shore A 80 polymer and a coloscope may use a Shore A 90 polymer, both of which are difficult to process with cutting tools due to their softness, particularly the Shore A 80 polymers. As used herein, the hardness of the polymer refers to the hardness of the raw material according to ASTM 2240. The final product is not tested according to ASTM 2240 because it lacks the physical dimensions required by the test method, e.g. minimum thickness of the material that is measured. Other, harder or softer, polymers may be used in the outer tube (or outer layer of the flexible tube).

In some embodiments, the method may comprise reducing, prior to providing said flexible tube, a radial cross-section area of the second section from an initial size to the second radial cross-section area.

Reducing a radial cross-section area of the second section may comprise grinding an outer surface of the second section. Belt or disk or wheel grinders may be used. Belt or disk or wheel grinders may be used to reduce the cross-sections of the second and/or the intermediate sections.

In addition to or alternatively to grinding, chemicals may be used to reduce the initial outer radial cross-section of the second section, for example by dipping.

Furthermore, an escomatic lathe may be used to both reduce the second section and an intermediate section between the first section and the second section, providing two steps. Advantageously, the escomatic lathe permits use of a coil of tubing and cutting the tubing into discrete flexible tubes of a predetermined length while also cutting the intermediate and second sections to their desired outer radial cross-sections, e.g. outer diameters.

A sleeve may be slid over the intermediate section and the bending section. The sleeve may be sealed at both ends to seal the bending section. In FIG. 11b, the proximal outer edge surface 43i abuts the tubular sleeve 100.

Figure 12A:
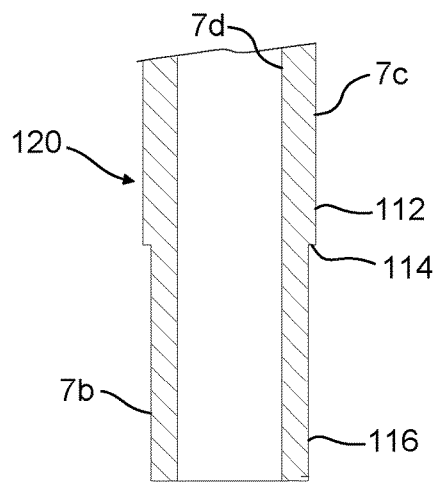
Figure 12C:
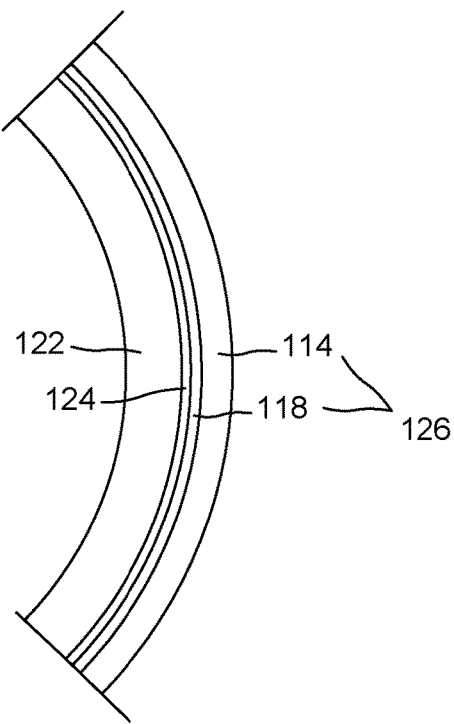
Figure 12B:
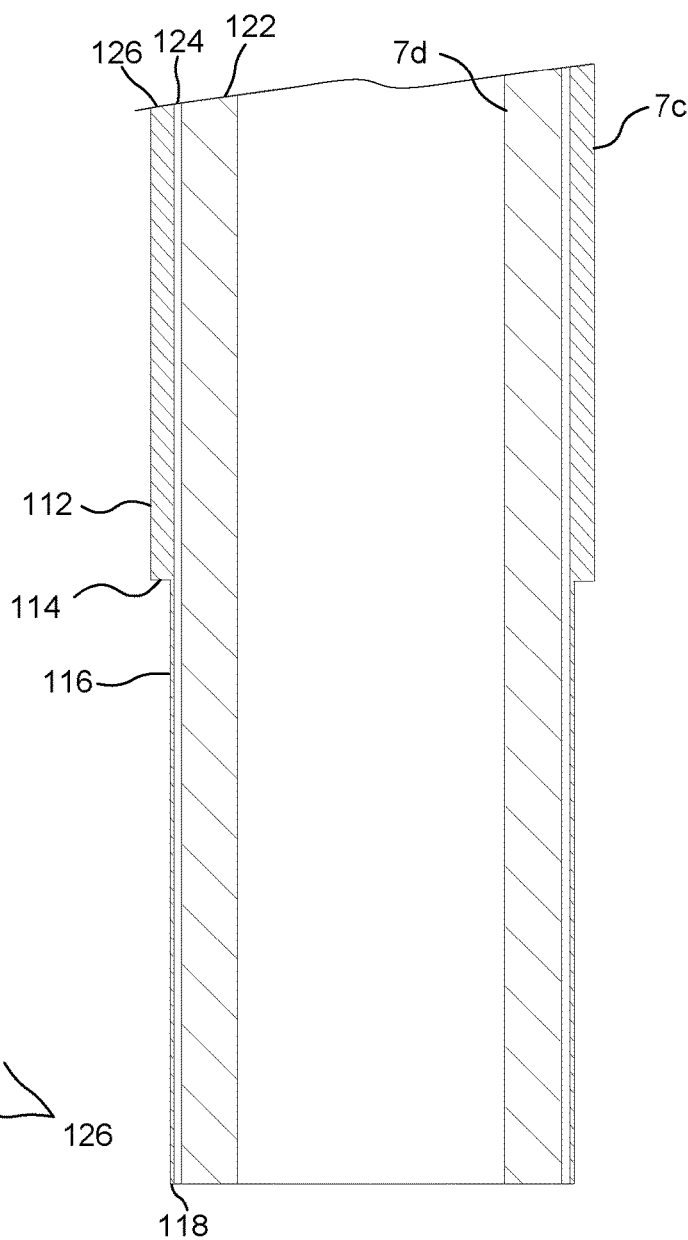
Figure 14A:
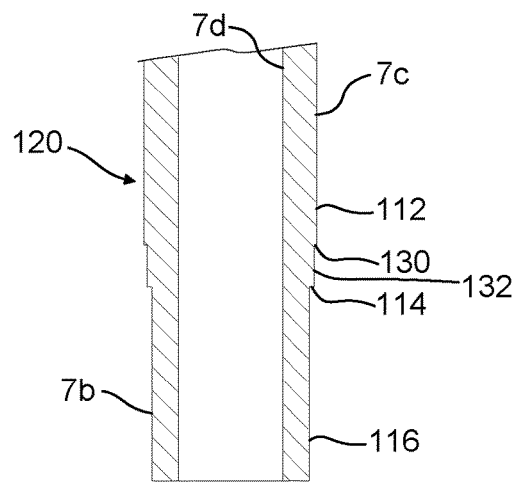
Figure 14B:
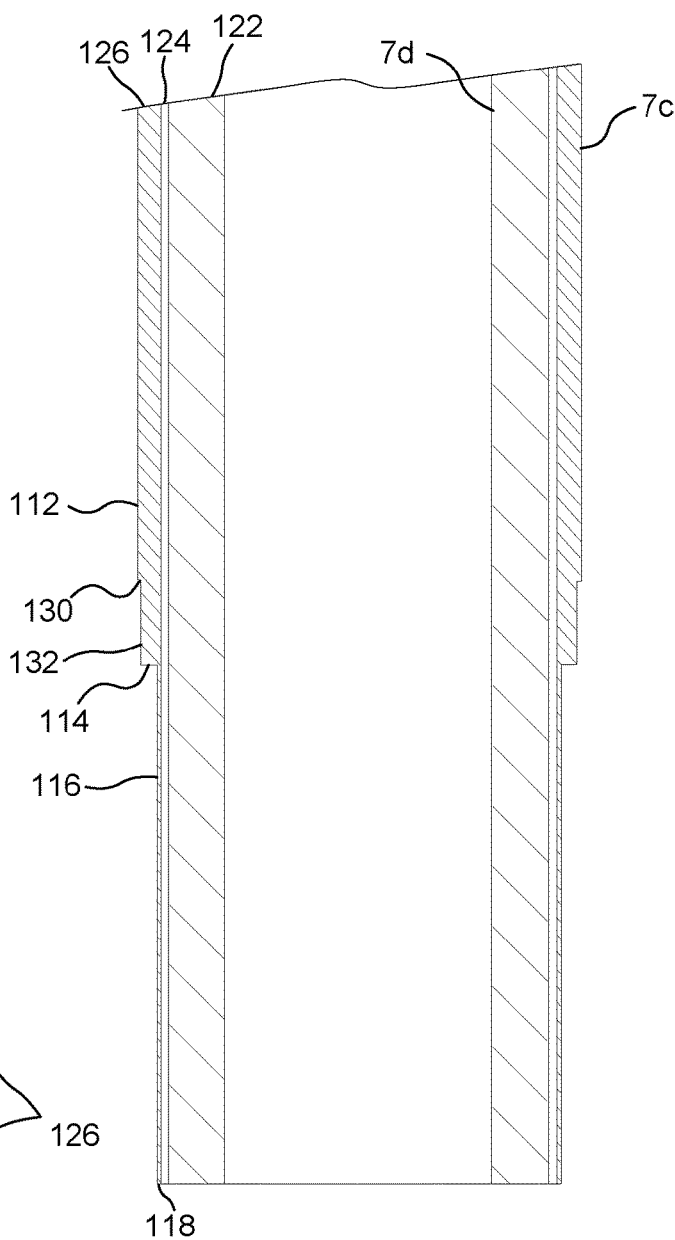
Figure 14C:
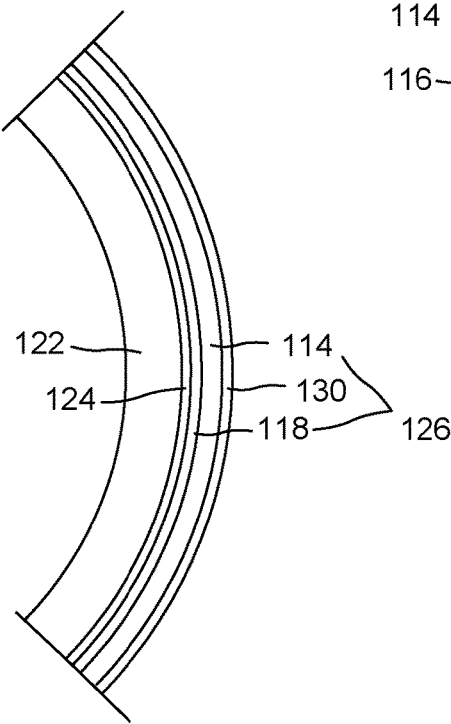

In the present variation, the circumferentially extending side wall 7a comprises a first section 112 having a first radial cross-section area and a second section 116 having a second radial cross-section area smaller than the first radial cross-section area, forming a first step 114 therebetween. Because both sections are formed a common the inner layer or tube, both sections are ring shaped with an equally sized circular opening at the center of the cross-section area. The first section 112 may extend to the handle. The cross-sections may be circular, oval, or have other shapes. The cross-sections are taken perpendicularly to a longitudinal axis of the flexible tube. The outer surface 7c includes, therefore, a first section outer surface and second section outer surface. The second section outer surface is sized and shaped to fit into the spacing 43c and be bonded to the proximal end segment of the bending section, as described above. The first section outer surface may be sized to be substantially flush with the outer surface of the proximal end of the proximal end segment, as shown in FIGS. 11a and 11b. Slight cross-sectional differences are also permissible, for example +/−5%, 10%, 20%, or 30% in the radius or radii (in case of non-circular cross-sections) of the respective outer surfaces. FIG. 12c is a sectional view from the distal end of the flexible tube. The distal end of the second section 116 is depicted as a distal surface 118 in FIGS. 12b and 12c. FIG. 11b illustrates the sleeve 100 positioned over the bending section distally of the proximal end of the proximal end segment. In the present example, the outer surface of the sleeve 100 is substantially flush with the outer surface of the distal end of the distal end segment.

Turning to FIGS. 13a, 13b, and 14a-c, the flexible tube 7 is depicted as flexible tube 120 to illustrate variations of the foregoing embodiments. The circumferentially extending side wall 7a comprises the first section 112 having the first radial cross-section area and an intermediate section 132 having an intermediate radial cross-section area smaller than the first radial cross-section area, forming an intermediate, or second, step 130 therebetween. The outer surface 7c includes, therefore, a first section surface, second section surface, and an intermediate surface between the first section surface and the second section surface. The second section surface is sized and shaped to fit into the spacing 43c and be bonded to the proximal end segment of the bending section, as described above. FIG. 13b illustrates the sleeve 100 positioned over the bending section and the intermediate section 132. In the present example, the outer surface of the sleeve 100 is substantially flush with the outer surface of the flexible tube 120, which is the first section surface. Slight cross-sectional differences are also permissible, for example +/−5%, 10%, 20%, or 30% in the diameter of the respective outer surfaces.

The second step 130 may be referred to as the proximal outer edge surface in the present embodiment, because the tubular sleeve 100 is slid over the intermediate section 132 until it is adjacent to or abuts the proximal outer edge surface 43i, such that the proximal end of the tubular sleeve and the proximal end of the proximal end segment present a uniform outer surface, albeit with a small or no gap between the proximal outer edge surface and the tubular sleeve. The first step 114 provides the same functionality with respect to proximal end of the proximal end segment, which may abut or be closely adjacent to the first step 114.

Figure 15A:
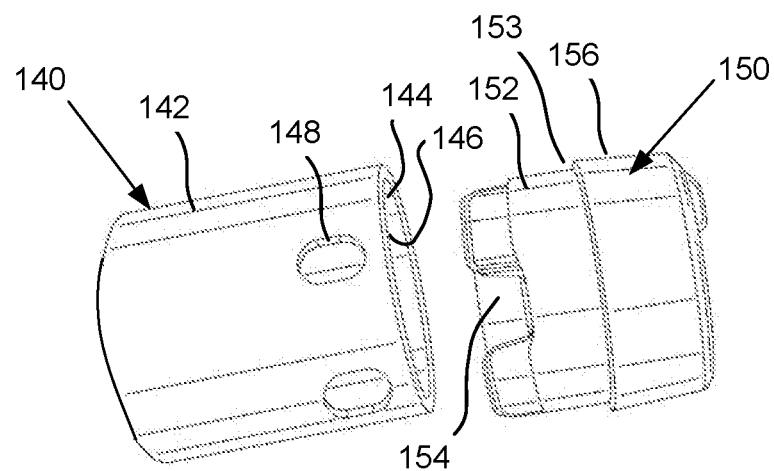
Figure 15B:
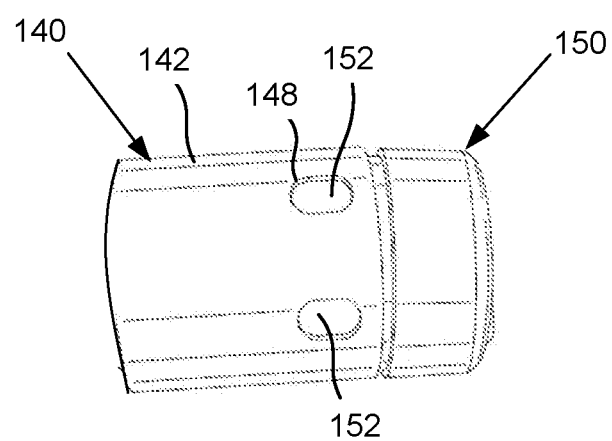

FIGS. 15a and 15b are perspective views of another embodiment of bending section 4 with a front end cap 150 of a medical device operable to obtain images of an internal cavity of a patient. The medical device may be an endoscope, duodenoscope, ENT scope etc. The medical device comprises a handle (not shown); a flexible tube (not shown) having a proximal end adjacent the handle and a distal end, the distal end of the flexible tube having an outer surface. Bending section 4 extends from the flexible tube and includes a proximal end segment, a distal end segment 140, and intermediate segments 42 between the proximal end segment and distal end segment 140, the intermediate segments hingedly connected to each other.

Distal end segment 140 includes a distal end segment peripheral wall 142 defining an internal space 144, the distal end segment peripheral wall having an inner surface 146 and including a cavity 148 extending radially outwardly from the inner surface.

Front end cap 150 has a proximal outer surface 152, and a distal outer surface 156. A camera assembly (not shown) is housed at least partly in a spacing 154 of front end cap 150. The proximal outer surface 152 may be a cylindrical surface. The front end cap 150 may be constructed from a polycarbonate material and may have an SFE greater than 42, more preferrably greater than 44. During assembly, front end cap 150 is positioned at least partly in the internal space of distal end segment peripheral wall 142 with cavity 148 overlapping outer surface 152 (best seen in FIG. 15b). An adhesive (not shown) is applied which bonds to outer surface 152 and penetrates cavity 148 to form a protrusion therein. The protrusion, also referred as a barb, secures front end cap 150 to distal end segment 140.

In one variation, the proximal end segment includes a proximal end segment peripheral wall defining an internal space, the proximal end segment peripheral wall having an inner surface and including a cavity extending radially outwardly from the inner surface, and the distal end of the flexible tube is positioned at least partly in the internal space of the proximal end segment peripheral wall with the cavity overlapping the outer surface. Another protrusion of adhesive bonded to the outer surface of the flexible tube extends into the cavity of the proximal end segment peripheral wall.

In another variation of the present embodiment, the distal end segment peripheral wall further comprises centering ribs extending radially inwardly from the inner surface and abutting the outer surface of the front end cap.

In another variation of the present embodiment, the bending section consists essentially of polypropylene (PP), polyethylene (PE), or polyoxymethylene (POM), and a solid surface free energy at 20° C. (SFE) of the bending section at the inner surface of the distal end segment peripheral wall is smaller than an SFE of the front end cap at the outer surface. In one example, the SFE of the bending section at the inner surface is at least 5 mN/m less than the SFE of front end cap at the outer surface.

In another variation of the present embodiment, cavity 148 is a through-hole with a major axis aligned with a longitudinal axis of the bending section and a minor, smaller, axis perpendicular to the major axis.

The inner surface of the distal end segment peripheral wall may have an SFE smaller than an SFE of the front end cap at the outer surface.

In another variation of the present embodiment, a second cavity (not shown) extends radially outwardly from the inner surface of the distal end segment peripheral wall, the second cavity having a periphery that is different than a periphery of the cavity. The cavity and the second cavity may have major axis orthogonal to each other to improve securement. Multiple cavities may be provided, as described previously.

A distal outer edge surface 153 is shown adjacent the distal outer surface 156. The tubular sleeve 100 may be slid over the distal end segment peripheral wall 142 and when the front end cap 150 is inserted into the distal end segment 140, the distal outer edge surface 153 may abut the distal end of the tubular sleeve, preventing that it slides off before it is adhesively bonded. The diameter of the distal outer surface 156 can be sized and shaped to provide a substantially uniform surface with the tubular sleeve.

Figure 16A:
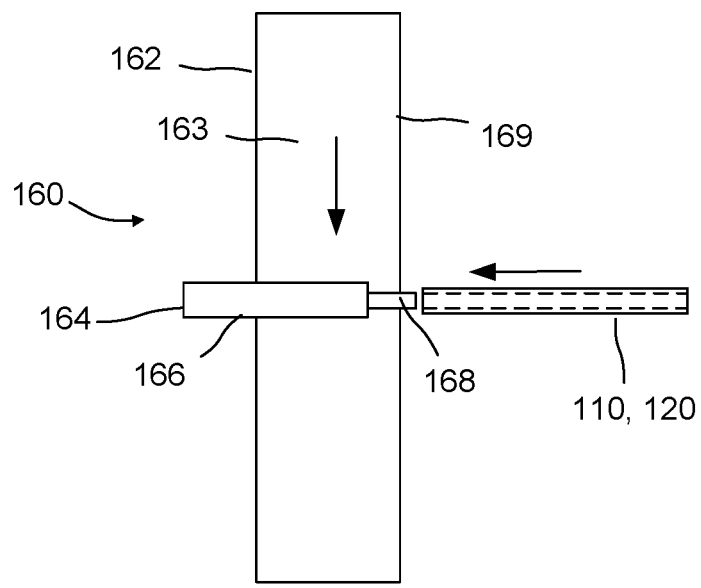
FIGS. 16a and 16b are depictions of an apparatus used to implement one embodiment of a method of making the flexible tubes described with reference to FIGS. 11a-14c.
Figure 16B:
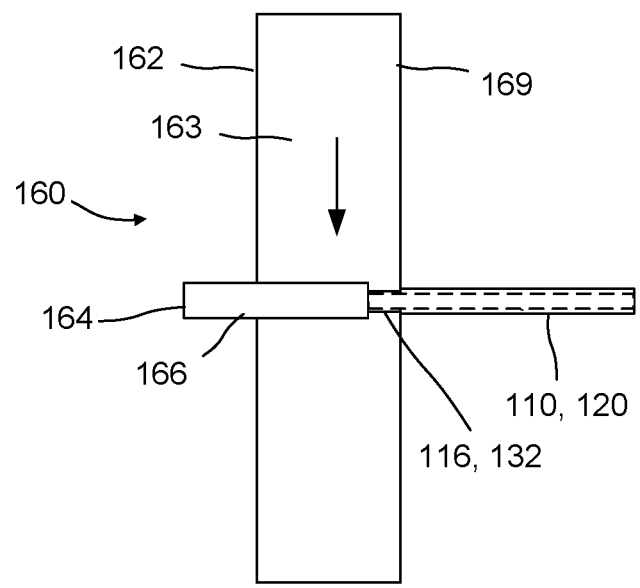

In another aspect of the present disclosure, an apparatus, depicted in FIGS. 16a and 16b, is provided to manufacture the flexible tubes depicted with reference to FIGS. 11a-14c. The apparatus, e.g. a grinder 160, includes a rotating grinding wheel 162 and a mandrel 164 having a large outer diameter section 166 and a small outer diameter section 168. The small outer diameter section 168 is sized to fit snugly in the flexible tube 110, 120. The large outer diameter section 166 is sized to abut the distal surface 118 of the flexible tube 110, 120. The mandrel 164 is positioned relative to the grinding surface 163 of the grinding wheel 162 and the distal surface 169 of the grinding wheel 162 to define the length of the second section 116 and the depth or size of the first step 114. Another mandrel, with a larger small outer diameter section 168, can be used to define the intermediate step 130.

In an alternative embodiment, one mandrel can be used with a grinding wheel that includes a step, thereby permitting grinding of the intermediate section and the second section in one operational step.

Further embodiments of the invention are disclosed in the below enumerated embodiments.

1. An articulated tip part for an endoscope, comprising a bending section having a number of hingedly connected segments including a proximal end segment, a distal end segment, and a plurality of intermediate segments positioned between the proximal end segment and the distal end segment, wherein at least one of the end segments comprises a number of at least one depression or through holethrough-hole being provided in an outer circumferentially extending side wall of the respective end segment, the side wall enclosing a spacing of the proximal end segment, a hardened adhesive adhering at least to a surface of another, separate member of the tip part and extending into the at least one depression or through holethrough-hole, so that the hardened adhesive in the at least one depression or through holethrough-hole forms a barb so as to secure the respective end segment to the other member of the tip part.

2. An articulated tip part according to embodiment 1, further comprising a flexible tube, wherein the proximal end segment comprises a first connection set including a number of depressions or through holesthrough-holes, the first connection set being provided in an outer circumferentially extending side wall of the proximal end segment, a hardened adhesive adhering at least to a surface of the flexible tube of the tip part and extending into the first connection set, so that the hardened adhesive in the first connection set forms a barb so as to secure the proximal end segment to the flexible tube.

3. An articulated tip part according to embodiment 1, further comprising a cap, wherein the distal end segment comprises a second connection set including a number of depressions or through holesthrough-holes, the second connection set being provided in an outer circumferentially extending side wall of the distal end segment, a hardened adhesive adhering at least to a surface of the cap of the tip part and extending into the second connection set, so that the hardened adhesive in the second connection set forms a barb so as to secure the distal end segment to the cap.

4. An articulated tip part according to embodiment 2, wherein the hardened adhesive in the connection set forms a positive engagement or connection to secure the respective end segment to the other member of the tip part, potentially preventing axial movement between the other member and the respective end segment.

5. An articulated tip part according to embodiment 1, wherein the other member of the tip part and the respective end segment are positioned adjacently.

6. An articulated tip part according to embodiment 1, wherein the other member of the tip part and the respective end segment are positioned with an overlap, and the connection set is in communication, potentially direct communication, with the overlap or is positioned adjacently to the overlap.

7. An bendable articulated tip part according to embodiment 2, wherein the connection set comprises at least one group of at least two depressions or through holesthrough-holes being interconnected by a recess provided in the outer circumferentially extending side wall of the respective end segment, the hardened adhesive adhering at least to the surface of the other member of the tip part and extending from the surface into each respective group of depressions or through holesthrough-holes of the connection set and into the recess interconnecting the respective group, thereby forming an anchor so as to secure the respective end segment to the other member of the tip part.

8. An articulated tip part according to embodiment 1, wherein the number of intermediate segments is at least 8, 9, 10, 11, 12, 13, 14, 15, 16, 17, 18, 19, 20, 21, 22, 23, 24, 25, 26, 27, 28, 29, or 30.

9. An articulated tip part according to embodiment 1, wherein the respective end segment encloses or surrounds, potentially completely encloses or surrounds, the other member of the tip part.

10. An articulated tip part according to embodiment 1, wherein the bending section comprises, or consists essentially of, polypropylene (PP), polyethylene (PE), or polyoxymethylene (POM).

11. An articulated tip part according to embodiment 1, wherein at least one of the end segments comprises at least one, two, three, or four centering ribs provided on an inner surface of the outer circumferentially extending side wall of the respective end segment, the centering ribs being positioned to abut an outer surface of the other member of the tip part so as to center the other member of the tip part in the spacing of the respective end segment.

12. An articulated tip part according to embodiment 11, wherein the proximal end segment of the tip part is attached to a distal end of a flexible tube, the flexible tube further comprising an opposite, proximal end, wherein the at least one end segment is the proximal end segment of the bending section, the proximal end segment comprising a number of at least one depression or through holethrough-hole being provided in an outer circumferentially extending side wall of the proximal end segment, the hardened adhesive adhering at least to an outer surface of the flexible tube and extending into the at least one depression or through holethrough-hole, so that the hardened adhesive in the at least one depression or through holethrough-hole forms a barb so as to secure the proximal end segment to the flexible tube, and wherein the proximal end segment has at least three centering ribs on an inner surface of the outer side wall of the proximal end segment, the centering ribs being positioned to abut an outer surface of the distal end of the flexible tube so as to center the flexible tube in the spacing of the proximal end segment.

13. An articulated tip part according to embodiment 12, wherein the proximal end segment has four centering ribs on the inner surface of the outer side wall of the proximal end segment, the centering ribs being positioned to abut an outer surface of the distal end of the flexible tube so as to center the flexible tube in the spacing of the proximal end segment.

14. An articulated tip part according to embodiment 12, wherein the tip part and the centering ribs extend in a longitudinal direction.

15. An articulated tip part according to embodiment 14, wherein the at least one hole or depression includes at least two holes or depressions, and wherein at least one of the centering ribs in the longitudinal direction extends between two of the holes or depressions.

16. An articulated tip part according to embodiment 12, wherein each centering rib in a circumferential direction extends less than or equal to 10 percent of a total circumferential extent of the inner surface of the outer circumferentially extending side wall of the respective end segment.

17. An articulated tip part according to embodiment 12, wherein each centering rib in a cross-sectional or radial direction extends less than or equal to 5 percent of a maximum cross-sectional extent of the inner surface of the outer circumferentially extending side wall of the respective end segment.

18. An articulated tip part according to embodiment 12, wherein the distal end of the flexible tube is inserted into the spacing of the proximal end segment of the bending section.

19. An articulated tip part according to embodiment 1, wherein at least one of, potentially all of, the number of depressions or through holesthrough-holes of the connection set has a non-sharp edge, preferably a rounded edge, bevelled edge, or chamfered edge.

20. An endoscope comprising an articulated tip part according to embodiments 1-19.

21. A system for visually inspecting inaccessible places such as human body cavities, the system comprising: an endoscope according to embodiment 20, and a monitor, wherein the endoscope is connectable to the monitor, and the monitor allows an operator to view an image captured by a camera assembly of the endoscope.

22. A method for securing a bending section to a flexible tube or a cap for at least partially assembling an articulated bendable tip part according to any one of embodiments 1-12, the method comprising the steps of: a. providing a bending section comprising a number of hingedly connected segments including a proximal end segment, a distal end segment, and a plurality of intermediate segments positioned between the proximal end segment and the distal end segment, at least one of the end segments comprises a number of at least one depression or through holethrough-hole, the connection set being provided in an outer circumferentially extending side wall of the respective end segment; b. providing another member of the tip part separate from the bending section; c. injecting an adhesive into the at least one depression or through holethrough-hole and into contact with a surface of the other member of the tip part; and d. allowing or causing the adhesive to harden, whereby the hardened adhesive forms a barb at least adhering to the other member so as to secure the respective end segment to the other member of the tip part.

23. A method according to embodiment 22, wherein the at least one of the end segments is the proximal end segment, wherein the proximal end segment has at least three centering ribs on an inner surface of the outer side wall of the proximal end segment, and wherein the other member of the tip part is a flexible tube having a proximal end and a distal end, the method further comprising the step of inserting the distal end of the flexible tube into the proximal end segment, the centering ribs being positioned to abut an outer surface of the distal end of the flexible tube so as to center the flexible tube in the spacing of the proximal end segment, the spacing being enclosed by the side wall, whereby the barb at least adheres to the flexible tube so as to secure the proximal end segment to the flexible tube.

24. An articulated tip part for an endoscope comprising: a bending section having a number of hingedly connected segments including a proximal end segment, a distal end segment, and a plurality of intermediate segments positioned between the proximal end segment and the distal end segment, and a flexible tube comprising a proximal end and a distal end, wherein the proximal end segment of the bending section comprises a number of at least one depression or through holethrough-hole being provided in an outer circumferentially extending side wall of the proximal end segment, the side wall enclosing a spacing of the proximal end segment, a hardened adhesive adhering at least to an outer surface of the flexible tube and extending into the at least one depression or through holethrough-hole, so that the hardened adhesive in the at least one depression or through holethrough-hole forms a barb so as to secure the proximal end segment to the flexible tube, and wherein the proximal end segment has at least three centering ribs on an inner surface of the outer side wall of the proximal end segment, the centering ribs being positioned to abut an outer surface of the distal end of the flexible tube so as to center the flexible tube in the spacing of the proximal end segment.

25. A steerable videoscope, comprising: a bending section having a distal end and segments including a proximal end segment, a distal end segment, and intermediate segments positioned between the proximal end segment and the distal end segment, the segments being hingedly connected to each other, at least one of the segments including an outer surface having an area profile with a two-dimensional arithmetical mean height parameter, Sa, of at least 0.9 microns; and a tubular sleeve covering the intermediate segments.

26. The videoscope of embodiment 25, wherein the Sa in the range of 0.9 microns to 9.0 microns as measured by standard ISO 25178.

27. The videoscope of embodiment 26, wherein the Sa is in the range of 1.8 microns to 4.5 microns as measured by the ISO 25178 standard.

28. The videoscope of embodiment 27, wherein Sa is in the range of 1820 nanometers to 2860 nanometers as measured by the ISO 25178 standard.

29. The videoscope of embodiment 25, wherein each of the intermediate segments has an outer surface with an Sa in the range of 0.9 microns to 9.0 microns.

30. The videoscope of embodiment 29, further comprising a proximal outer edge surface and a distal outer edge surface, wherein the tubular sleeve has a proximal end with a proximal rim surface facing the proximal outer edge surface and a distal end with a distal rim surface facing the distal outer edge surface, the proximal outer edge surface and the distal outer edge surface preventing displacement of the tubular sleeve from the bending section.

31. The videoscope of embodiment 29, further comprising a handle with an articulation lever, and steering wires extending from the articulation lever through the bending section to the distal end segment, wherein actuation of the articulation lever causes the steering wires to bend the bending section along a bending plane.

32. The videoscope of embodiment 31, wherein the outer surfaces with the Sa in the range of 0.9 microns to 9.0 microns of each of the intermediate sections traverse the articulation plane to enable the tubular sleeve to slide on the outer surfaces of the intermediate segments.

33. The videoscope of embodiment 31, further comprising a flexible tube between the handle and the intermediate segments, wherein the proximal end segment has a proximal end comprising a bonding surface having an Sa of at least 0.9 microns, and wherein the flexible tube has a distal end bonded to the bonding surface of the proximal end of the proximal end segment.

34. The videoscope of embodiment 33, wherein the proximal end segment comprises the proximal outer edge surface.

35. The videoscope of embodiment 34, wherein the distal end of the flexible tube is positioned within the proximal end of the proximal end segment, and the bonding surface is an inner surface of the proximal end of the proximal end segment.

36. The videoscope of embodiment 33, wherein bonding surface is proximal of the tubular sleeve.

37. The videoscope of embodiment 7, further comprising a cap, wherein the distal end segment has a distal end comprising a bonding surface having an Sa of at least 0.9 microns, and wherein the cap has a proximal end bonded to the bonding surface of the distal end of the distal end segment.

38. The videoscope of embodiment 13, wherein the distal end segment comprises the distal outer edge surface.

39. The videoscope of embodiment 14, wherein the proximal end of the cap is positioned within the distal end of the distal end segment.

40. The videoscope of embodiment 15, wherein bonding surface is distal of the tubular sleeve.

41. The videoscope of embodiment 13, wherein the distal end of the distal end segment is positioned within the proximal end of the cap.

42. The videoscope of embodiment 25, further comprising a handle with an articulation lever, a flexible tube extending from the handle to the bending section, and a cap supported by the bending section, wherein the bending section further comprises flexible hinges connecting adjacent segments, the flexible hinges being integrally molded with the segments in a one-piece part.

43. The videoscope of embodiment 18, wherein the proximal end segment comprises a proximal circumferential wall forming a collar, a distal circumferential wall having a smaller diameter than the proximal circumferential wall, and a proximal outer edge surface between the proximal circumferential wall and the distal circumferential wall, and wherein the flexible tube comprises a distal end positioned within and affixed to the collar.

44. The videoscope of embodiment 19, wherein the diameter of the distal circumferential wall of the proximal end segment is equal to a diameter of an intermediate segment.

45. The videoscope of any one of embodiments 25-44, comprising an articulated tip part according to any one of embodiments 1-19.

46. A visualization system comprising: the videoscope of any one of embodiments 25-45, further comprising a camera assembly; and a monitor including a display screen, wherein the videoscope is connectable to the monitor and the monitor is operable to present images corresponding to image data provided by the camera assembly of the videoscope.

47. The visualization system of embodiment 46, wherein each of the intermediate segments has an outer surface with an Sa in the range of 0.9 microns to 9.0 microns.

48. A visualization system comprising: the videoscope of any one of embodiments 25-44; and a video processing apparatus with an output port adapted to communicatively couple to a monitor including a display screen, wherein the monitor is operable to present images corresponding to image data provided by the camera assembly of the videoscope.

49. The visualization system of embodiment 48, wherein each of the intermediate segments has an outer surface with an Sa in the range of 0.9 microns to 9.0 microns.

LIST OF REFERENCES

The following is a list of reference numerals used throughout this specification.

| # | Description |
|---|---|
| 1 | endoscope |
| 11 | monitor |
| 12 | cable socket |
| 13 | monitor cable |
| 2 | handle |
| 21 | control lever |
| 3 | insertion tube |
| 3a | proximal end |
| 3b | distal end |
| 4 | bending section |
| 41 | distal end segment |
| 41a | distal end |
| 41b | outer circumferentially extending side wall |
| 41c | spacing |
| 41d | opening |
| 41e | outer surface |
| 42 | intermediate segment |
| 43 | proximal end segment |
| 43a | proximal end |
| 43b | outer circumferentially extending side wall |
| 43c | spacing |
| 43d | opening |
| 43e | outer surface |
| 43f | centering rib |
| 43g | distal end |
| 43h | inner surface |
| 43i | proximal outer edge surface |
| 5 | tip part |
| 6 | cap |
| 6a | circumferentially extending side wall |
| 6b | proximal end |
| 6c | proximal cap end |
| 6d | cap end surface |
| 6e | protrusions 6e |
| 61 | camera assembly |
| 7 | flexible tube |
| 7a | circumferentially extending side wall |
| 7b | distal end |
| 7c | outer surface |
| 7d | inner surface |
| 8 | hardened adhesive |
| 8a | first portion of hardened adhesive |
| 8b | second portion of hardened adhesive |
| 91 | first connection set |
| 91a | first through-hole |
| 91b | second through-hole |
| 91c | third through-hole |
| 91d | fourth through-hole |
| 92 | second connection set |
| 93 | first group |
| 93a | through-hole |
| 93b | recess |
| 94 | second group |
| 94a | through-hole |
| 94b | recess |
| 95 | third group |
| 95a | through-hole |
| 95b | recess |
| 96 | rounded edge |
| PD | proximal-distal axis |
| 100 | sleeve |
| 110 | flexible tube |
| 112 | first section |
| 114 | first step |
| 116 | second section |
| 118 | distal surface |
| 120 | flexible tube |
| 122 | inner tube |
| 124 | intermediate tube |
| 126 | outer tube |
| 130 | intermediate step |
| 132 | intermediate section |
| 140 | distal end segment |
| 142 | peripheral wall |
| 144 | spacing, internal space |
| 146 | inner surface |
| 148 | cavity |
| 150 | front end cap |
| 152 | proximal outer surface |
| 153 | distal outer edge surface |
| 154 | spacing |

| # | Description |
|---|---|
| 156 | distal outer surface |
| 160 | grinder |
| 162 | grinder wheel |
| 163 | grinding surface |
| 164 | mandrel |
| 166 | large outer diameter section |
| 168 | small outer diameter section |
| 169 | distal surface |

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A medical device operable to obtain images of an internal cavity of a patient, the medical device comprising:
   a handle;
   a flexible tube having a proximal end adjacent the handle and a distal end, the flexible tube including a first section having a first radial cross-section area and a second section distal of the first section and having a second radial cross-section area smaller than the first radial cross-section area, the second section having a cylindrical outer surface extending along an entire length of the second section;
   a bending section extending from the flexible tube and including hinges and segments formed together with the hinges as a single part, the segments comprising a proximal end segment, a distal end segment, and intermediate segments between the proximal end segment and the distal end segment, the segments hingedly connected to each other by the hinges, the proximal end segment including a proximal end segment peripheral wall having an inner surface defining an internal space, the second section positioned at least partly in the internal space, wherein the intermediate segments include outer surfaces, wherein at least some of the outer surfaces of the intermediate sections segments comprise an area profile with a two-dimensional arithmetical mean height parameter, Sa, in the range of 0.9 microns to 9.0 microns as measured by standard ISO 25178;
   a tubular sleeve disposed over the bending section; and
   a camera assembly supported by the bending section and operable to generate images of distal views,
   wherein the at least some of the outer surfaces comprising the Sa in the range of 0.9 microns to 9.0 microns traverse an articulation plane to enable the tubular sleeve to slide on the outer surfaces of the segments, and
   wherein the bending section comprises a proximal outer edge surface, and
   wherein the tubular sleeve comprises a proximal end with a proximal rim surface facing the proximal outer edge surface.

2. The medical device of claim 1, wherein the proximal end segment peripheral wall comprises a cavity extending radially outwardly from the inner surface and overlapping the outer surface of the second section, further comprising a hardened adhesive bonded to the outer surface of the second section and extending into the cavity to affix the bending section to the flexible tube.

3. The medical device of claim 1, wherein the flexible tube further comprises an intermediate section between the first section and the second section, the intermediate section having an intermediate radial cross-section area smaller than the first radial cross-section area and larger than the second radial cross-section area.

4. The medical device of claim 3, wherein the tubular sleeve is disposed over the bending section and the intermediate section of the flexible tube.

5. The medical device of claim 1, further comprising a front end cap housing the camera assembly and having a proximal outer surface and a distal outer surface, wherein the distal end segment includes a distal end segment peripheral wall having an inner surface defining an internal space and including a cavity extending radially outwardly from the inner surface, the front end cap positioned at least partly in the internal space of the distal end segment peripheral wall with the cavity overlapping the proximal outer surface, further comprising a second hardened adhesive bonded to the proximal outer surface of the front end cap and extending into the cavity of the distal end segment peripheral wall.

6. The medical device of claim 1, wherein the Sa is in the range of 1.8 microns to 4.5 microns as measured by the ISO 25178 standard.

7. The medical device of claim 1, wherein the flexible tube further comprises an intermediate section between the first section and the second section, the intermediate section having an intermediate radial cross-section area smaller than the first radial cross-section area and larger than the second radial cross-section area, wherein the tubular sleeve is disposed over the bending section and the intermediate section of the flexible tube, and wherein the proximal outer edge surface is located between the first section and the intermediate section.

8. The medical device of claim 1, wherein the proximal end segment comprises a cavity extending radially outwardly from the inner surface, the second section positioned with the cavity overlapping the outer surface of the second section,
   the medical device further comprising a hardened adhesive bonded to the outer surface of the second section and extending into the cavity to affix the bending section to the flexible tube, the cavity comprising a through-hole having a closed perimeter.

9. The medical device of claim 8, wherein the flexible tube comprises a multi-layered structure including a coil and a polymeric layer enclosing the coil, wherein a radial cross-section area of the coil is smaller than the second radial cross-section area, and wherein the outer surface of the second section is formed of the polymeric layer.

10. The medical device of claim 9, wherein the flexible tube further comprises an intermediate section between the first section and the second section, the intermediate section having an intermediate radial cross-section area smaller than the first radial cross-section area and larger than the second radial cross-section area, wherein the tubular sleeve is disposed over the bending section and the intermediate section of the flexible tube.

11. The medical device of claim 8, further comprising a front end cap housing an image sensor of the camera assembly and having a proximal outer surface and a distal outer surface with the distal outer edge surface therebetween, wherein the distal end segment includes a distal end segment peripheral wall having an inner surface defining an internal space and including a cavity extending radially outwardly from the inner surface, the front end cap positioned at least partly in the internal space of the distal end segment peripheral wall with the cavity overlapping the proximal outer surface, further comprising a second hardened adhesive bonded to the proximal outer surface of the front end cap and extending into the cavity of the distal end segment peripheral wall.

12. The medical device of claim 1, wherein the proximal end segment and the distal end segment comprise outer peripheral surfaces with an area profile comprising an Sa of at least 0.9 microns.

13. The medical device of claim 1, wherein the Sa of the at least some of the outer surfaces of the intermediate segments is at least 2.34+/−0.52 microns.

14. The medical device of claim 1, wherein the bending section consists essentially of polyoxymethylene.

15. The medical device of claim 14, wherein the outer surface of the second section of the flexible tube has an Sa greater than 2.34 +/−0.52 microns.

16. The medical device of claim 1, wherein the bending section consists essentially of polyoxymethylene, and wherein the proximal end segment and the distal end segment comprise outer peripheral surfaces with an area profile comprising an Sa of at least 2.34+/−0.52 microns.

17. The medical device of claim 1, wherein the proximal end segment peripheral wall comprises through-holes distributed circumferentially and extending from the inner surface through the peripheral wall, wherein each of the through-holes comprises a closed perimeter, the medical device further comprising a hardened adhesive bonded to the outer surface of the second section of the flexible tube and extending into the through-holes of the proximal end segment to affix the bending section to the flexible tube.

18. The medical device of claim 1, wherein the proximal end segment peripheral wall comprises a plurality of non-overlapping cavities each extending radially outwardly from the inner surface of the proximal end segment and overlapping the outer surface of the second section, further comprising a hardened adhesive bonded to the outer surface of the second section and extending into each of the plurality of non-overlapping cavities to affix the bending section to the flexible tube.

* * * * *